US006420335B1

(12) United States Patent
Weichselbaum et al.

(10) Patent No.: US 6,420,335 B1
(45) Date of Patent: Jul. 16, 2002

(54) COMBINATION OF RADIOTHERAPY AND ANTI-ANGIOGENIC FACTORS

(75) Inventors: Ralph R. Weichselbaum, Chicago, IL (US); Vikas P. Sukhatme, Newton; Donald W. Kufe, Wellesley, both of MA (US)

(73) Assignees: Dana Farber Cancer Institute, Inc., Boston, MA (US); ARCH Development Corporation, Chicago, IL (US); Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 09/334,084

(22) Filed: Jun. 16, 1999

Related U.S. Application Data

(60) Provisional application No. 60/125,566, filed on Mar. 23, 1999, and provisional application No. 60/089,218, filed on Jun. 15, 1998.

(51) Int. Cl.[7] .......................... A01N 37/18; A01N 5/10; A01N 61/00; A01N 5/00; C07K 1/00

(52) U.S. Cl. ............................ 514/2; 530/350; 378/65; 514/1; 600/1

(58) Field of Search ........................... 514/2, 1; 378/65; 530/300, 350; 600/1

(56) References Cited

U.S. PATENT DOCUMENTS

| | | | |
|---|---|---|---|
| 5,563,160 A | 10/1996 | Bramm et al. | 514/353 |
| 5,639,725 A | 6/1997 | O'Reilly et al. | 514/12 |
| 5,733,876 A | 3/1998 | O'Reilly et al. | 514/12 |
| 5,854,205 A | 12/1998 | O'Reilly et al. | 514/2 |
| 6,140,246 A | * 10/2000 | Andrulis, Jr. et al. | 514/323 |
| 6,169,104 B1 | * 1/2001 | Tuse' et al. | 514/405 |

FOREIGN PATENT DOCUMENTS

| | | |
|---|---|---|
| EP | 0273085 | 7/1988 |
| JP | 09025268 | 1/1997 |
| WO | WO 95/29242 | 11/1995 |
| WO | WO 96/35774 | 4/1996 |

OTHER PUBLICATIONS

Mauceri et al., "Combined effects of angiostatin and ionizing radiation in antitumor therapy," *Nature*, 394(6690):287–291, 1998.
Tanaka et al., "Viral vector–targeted antiangiogenic gene therapy utilizing an angiostatin complementary DNA," *Cancer Res.*, 58(15):3362–3369, 1998.
Cao et al., "Kringle domains of human angiostatin," *J. Biol. Chem.*, 271:29461–29467, 1996.
Fidler and Ellis, "The implications of angiogenesis for the biology and therapy of cancer metastasis," *Cell*, 79:185–188, 1994.

Fidler, "Modulation of the organ microenvionment for treatment of cancer metastasis," *J. Natl. Cancer Inst.*, 87:1588, 1995.
Folkman and Shing, "Angiogenesis," *J. Biol. Chem.*, 267:10931–10934, 1992.
Folkman, "How is blood vessel growth regulated in normal and neoplastic tissue?," *Cancer Res.* 46, 467–473, 1986.
Folkman, "Successful treatment of an angiogenic disease," *N Engl J Med.* 320(18): 1211–1212, 1989.
Hohenester et al., "Crystal structure of the angiogenesis inhibitor endostatin at 1.5 Å resolution," *EMBO J.*, 17:1656–1664.
Kerbel, "Inhibition of tumor angiogenesis as a strategy to circumvent required resistance to anti–cancer therapeutic agents," *Bioassays*, 13:31–36, 1991.
Klagsbrun and D'Amore, "Regulators of angiogenesis," *Annual Rev. Physiol.*, 53:217–239, 1991.
O'Reilly et al., "Endostatin: an endogenous inhibitor of angiogenesis and tumor growth," *Cell*, 88:277–285, 1997.
O'Reilly et al., "Angiostatin: a novel angiogenesis inhibitor that mediates the suppression fo metastases by a Lewis lung carcinoma," *Cell*, 79:315–328, 1994.
Sim et al., "A recombinant human angiostatin protein inhibits experimental primary and metastatic cancer," *Cancer Res.*, 57:1329–1334, 1997.
Weichselbaum et al. "Radiation–resistant and repair–proficient human tumor cells may be associated with radiotherapy failure in head– and neck–cancer patients,", *Proc. Natl. Acad. Sci. USA*, 83:2684–2688, 1986.
Weichselbaum et al., "Gene therapy targeted by ionizing radiation," *Int. J. Radiant Oncol. Biol. Phys.*, 24:565–567, 1992.
Weichselbaum et al., "Heterogeneity of radiation response of a parent human epidermoid carcinoma cell line and four clones," *Int. J. Radiat. Oncol. Biol. Phys.*, 14:907–912, 1988.
Weidner et al., "Tumor angiogenesis correlates with metastasis in invasive prostate carcinoma," *Am J Pathol*;143:400–409, 1993.
Weidner et al., "Tumor angiogenesis and metastasis–correlation in invasive breast carcinoma," *N Engl J Med*;324:1–8, 1991.
Weidner, "Tumoural vascularity as a prognostic factor in cancer patients: the evidence continues to grow," *J. Pathol.*, 184:119–122, 1998.

* cited by examiner

*Primary Examiner*—Scott D. Priebe
*Assistant Examiner*—Shin-Lin Chen
(74) *Attorney, Agent, or Firm*—Fulbright & Jaworski

(57) ABSTRACT

The present invention relates generally to the fields of angiogenesis and cancer therapy. More particularly, it concerns the use of anti-angiogenic factors in cancer therapy. The present invention demonstrates that angiostatin or endostatin can sensitize a cell to radiation therapy. Methods and compositions for inhibiting growth, sensitizing a cell to radiotherapy and treating cancer growth by first inhibiting angiogenesis and then employing radiotherapy are described.

28 Claims, 11 Drawing Sheets

COMBINATION OF RADIOTHERAPY AND ANTI-ANGIOGENIC FACTORS

This application claims priority to and specifically incorporates by reference, the content of U.S. Provisional Application Serial No. 60/089,218 filed Jun. 15, 1998 and U.S. Provisional Application Serial No. 60/125,566 filed Mar. 23, 1999. The entire text of each of the above-referenced disclosures is specifically incorporated by reference herein without disclaimer.

The government owns rights in the present invention pursuant to grant number CA41068 from the National Instiues of Health.

BACKGROUND OF THE INVENTION

1. Field of the Invention

The present invention relates generally to the fields of neovascularization and cancer therapy. More particularly, it concerns the methods and compositions for treating cancer growth by first inhibiting angiogenesis and then employing radiotherapy.

2. Description of Related Art

Normal tissue homeostasis is achieved by an intricate balance between the rate of cell proliferation and cell death. Disruption of this balance either by increasing the rate of cell proliferation or decreasing the rate of cell death can result in the abnormal growth of cells and is thought to be a major event in the development of cancer. The effects of cancer are catastrophic, causing over half a million deaths per year in the United States alone. Conventional strategies for the treatment of cancer include chemotherapy, radiotherapy, surgery, biological therapy or combinations thereof; however further advances in these strategies are limited by lack of specificity and excessive toxicity to normal tissues. In addition, certain cancers are refractory to treatments such as chemotherapy, and some of these strategies such as surgery are not always viable alternatives.

Once the diagnosis of cancer is established, the most urgent question is whether the disease is localized, or has spread to lymph nodes and distant organs. The most fearsome aspect of cancer is metastasis, and this fear is well justified. In nearly 50% of patients, surgical excision of primary neoplasms is ineffective, because metastasis has occurred by the time the tumor is large enough for resection (Sugarbaker, 1977; Fidler and Balch, 1987). Metastases can be located in different organs and in different regions of the same organ, making complete eradication by surgery, radiation, drugs, or biotherapy difficult. Furthermore, the organ microenvironment significantly influences the response of tumor cells to therapy (Fidler, 1995), as well as the efficiency of anticancer drugs, which must be delivered to tumor foci in amounts sufficient to destroy cells without leading to undesirable side effects (Fidler and Poste, 1985). In addition, the treatment of metastatic cancer is greatly hindered due to the biological heterogeneity of cancer cells, and the rapid emergence of tumor cells that become resistant to most conventional anticancer agents (Fidler and Poste, 1985).

One of the processes involved in the growth of both primary and secondary (metastatic) tumors is neovascularization, or creation of new blood vessels which grow into the tumor. This neovascularization is termed angiogenesis (Folkman, 1986, 1989), which provides the growing tumor with a blood supply and essential nutrients. Although tumors of 1–2 mm in diameter can receive all nutrients by diffusion, further growth depends on the development of an adequate blood supply through angiogenesis. Inhibition of angiogenesis provides a novel and more general approach for treating both primary and secondary tumors by manipulation of the host microenvironment.

The induction of angiogenesis is mediated by several angiogenic molecules released by tumor cells, tumor associated endothelial cells and the normal cells surrounding the tumor endothelial cells. The prevascular stage of a tumor is associated with local benign tumors, whereas the vascular stage is associated with tumors capable of metastasizing. Moreover, studies using light microscopy and immunohistochemistry concluded that the number and density of microvessels in different human cancers directly correlate with their potential to invade and produce metastasis (Weidner et al., 1991, 1993). Not all angiogenic tumors produce metastasis, but the inhibition of angiogenesis prevents the growth of tumor endothelial cells at both the primary and secondary sites and thus can prevent the emergence of metastases.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

Persistent and unregulated angiogenesis is characteristic of tumor growth and it supports the pathological damage seen in these cancer. Thus, tumor growth is an angiogenesis-dependent process (Folkman, 1971). After an initial prevascular phase, every increase in tumor endothelial cell population is preceded by an increase in new capillaries converging on the tumor. Expansion of tumor volume beyond this phase requires the induction of new capillary blood vessels.

It has been demonstrated that in mice bearing Lewis lung carcinoma (3LL) subcutaneously (s.c.), the primary or local tumor releases an angiogenesis-inhibiting substance, named angiostatin (O'Reilly et al. 1994). Angiostatin is a 38-kDa fragment of plasminogen that selectively inhibits proliferation of endothelial cells. Angiostatin has been shown to suppresses vascularization and, hence, growth of metastases when used as an adjuvant to conventional therapy (U.S. Pat. No. 5,733,876, specifically incorporated herein by reference). Several studies have produced results consistent with this model. After systemic administration, purified angiostatin can produce apoptosis in metastases (Holmgren et al., 1995) and sustain dormancy of several human tumors implanted subcutaneously in nude mice (O'Reilly et al., 1996). However, although it is known that angiostatin can be generated in vitro from plasminogen by digestion with pancreatic elastase (O'Reilly, 1994), how it is generated in vivo in tumors remains unclear. Recently a second peptide, endostatin, was identified as a potential inhibitor of angiogenesis (O'Reilly et al., 1997). Endostatin, produced by hemangioendothelioma, is a 20 kDa C-terminal proteolytic fragment of collagen XVIII (Hohenester et al., 1998). Endostatin specifically inhibits endothelial proliferation and is postulated to inhibit angiogenesis and tumor growth.

Clearly, angiogenesis plays a major role in cancer development and maintenance. As stated earlier, conventional cancer therapeutic regimens are hampered by the ability of the cancer cell to adapt and become resistant to the therapeutic modality used to combat tumor growth. Although, it has been suggested that angiostatin may be useful in reducing the growth, size and otherwise mitigating the deleterious effect of a tumor, there is presently no objective evidence to suggest that angiostatin or endostatin could be used to weaken a tumor such that it would subsequently be amenable to radiotherapy.

SUMMARY OF THE INVENTION

Thus, the present invention provides a method of sensitizing a cell to ionizing radiation comprising the steps of first contacting the cell with an anti-angiogenic factor in an amount effective to sensitize the cell to ionizing radiation; and then exposing the cell to a dose of ionizing radiation effective to inhibit the growth of the cell.

In particularly preferred embodiments, the cell is an endothelial cell lining blood vessels that supply a tumor, defined hereafter as a tumor endothelial cell. In more defined embodiments, the tumor endothelial cell is located within an animal, and the contacting comprises in vivo delivery of the anti-angiogenic factor. In certain embodiments, the contacting is effected by direct injection of the tumor with the anti-angiogenic factor. In other embodiments, the contacting is effected by regional delivery of the anti-angiogenic factor. In still another embodiment, the contacting is effected by local delivery of the anti-angiogenic factor. In preferred embodiments, the anti-angiogenic factor may be delivered endoscopically, intratracheally, intralesionally, percutaneously, intravenously, subcutaneously or intratumorally.

In certain embodiments, the method may further comprise the step of tumor resection, prior to, after or during the contacting with the anti-angiogenic factor. In particularly defined embodiments, the anti-angiogenic factor is administered 2 days prior to the radiation. In other embodiments, the anti-angiogenic factor is administered 1 day prior to the radiation. In still another embodiment the anti-angiogenic factor is administered 12 hours prior to the radiation. In yet further embodiments, the anti-angiogenic factor is administered 6 hours prior to the radiation. In yet another embodiment, the anti-angiogenic factor is administered 3 hours prior to the radiation. In still another embodiment, the anti-angiogenic factor is administered 1 hour prior to the radiation. In yet another embodiment, the anti-angiogenic factor is administered 30 minutes prior to the radiation. In still another embodiment the anti-angiogenic factor is administered 15 minutes prior to the radiation. Another embodiment contemplates that the anti-angiogenic factor is administered immediately prior to the radiation. These are only exemplary embodiments, the time at which the anti-angiogenic factor is administered is only limited in the fact that it is administered prior to the administration of the radiation. Thus, the anti-angiogenic factor may be administered months, weeks, days, hours or minutes prior to the ionizing radiation. Further, the anti-angiogenic factor may be administered as a single dose, multiple doses over a measured period of time or as a continuous perfusion of the tumor. The time interval, time courses and doses of anti-angiogenic factor administration will depend on factors to be determined by the clinician. Such factors would take into account tumor size, other therapies being administered, condition of the patient and pharmacokinetic properties of the agent being administered.

The present invention provides methods of sensitizing cells to ionizing radiation by contacting the cells with an anti-angiogenic factor. In particular embodiments, the anti-angiogenic factor is angiostatin. In another embodiment, the anti-angiogenic factor is endostatin. In yet other embodiments, the cell is further sensitized to ionizing radiation by contacting the cell with the cytokine IL-12, in combination with an anti-angiogenic factor. In another embodiment, the cell is sensitized to ionizing radiation by contacting the cell with an antibody specific to VEGF, in combination with an anti-angiogenic factor.

In certain embodiments the tumor endothelial cell is a human tumor endothelial cell. In other more defined embodiments, the human tumor endothelial cell feeds a brain cancer cell. In other particularly preferred embodiments, the human tumor endothelial cell feeds a breast cancer cell. In certain embodiments, the tumor cell or tumor endothelial cell is resistant to anti-angiogenic factor therapy. In other embodiments, the tumor cell or tumor endothelial cell is resistant to radiotherapy.

In particular embodiments, the radiation employed may be ionizing radiation is X-radiation, γ-radiation, or β-radiation.

In certain embodiments, contacting the cell with the anti-angiogenic factor comprises contacting the cell with an expression construct comprising an anti-angiogenic factor encoding gene operatively linked to a promoter, wherein the promoter directs the expression of the anti-angiogenic factor in the cell. In more defined aspects, the expression construct is selected from the group consisting of an adenovirus, an adeno-associated virus, a vaccinia virus and a herpes virus. In other defined aspects, the contacting comprises in vivo delivery of the expression construct.

In other aspects of the present invention the methods may further comprise the step of contacting the cell with a chemotherapeutic agent. In preferred embodiments, the chemotherapeutic agent is selected from the group consisting of adriamycin, 5-fluorouracil (5FU), etoposide (VP- 16), camptothecin, actinomycin-D, mitomycin C, cisplatin (CDDP), doxorubicin, etoposide, verapamil, podophyllotoxin, carboplatin, procarbazine, mechlorethamine, cyclophosphamide, ifosfamide, melphalan, chlorambucil, bisulfan, nitrosurea, dactinomycin, daunorubicin, bleomycin, plicomycin, mitomycin, tamoxifen, taxol, transplatinum, vincristin, vinblastin and methotrexate.

Also contemplated by the present invention is a method for inhibiting growth of a cancer in a subject comprising the steps of first delivering to a cancer cell of the subject a therapeutically effective amount of a DNA molecule comprising a promoter operatively linked to an coding region that encodes an anti-angiogenic factor protein; and then exposing the cell to a dose of ionizing radiation; wherein the anti-angiogenic factor is delivered prior to the radiation and the expression of the anti-angiogenic factor sensitizes the cancer to the ionizing radiation and thereby inhibits the growth of the cancer.

In particularly defined embodiments, the promoter is a radiation responsive enhancer-promoter. It is contemplated that the delivering may be effected by regional delivery of the expression construct, local delivery of the expression construct, or direct injection of a tumor with the expression construct.

It is particularly contemplated that the contacting may comprise delivering the expression construct endoscopically, intratracheally, intralesionally, percutaneously, intravenously, subcutaneously or intratumorally.

In additional embodiments, the method may further comprise the step of tumor resection, prior to the contacting. Other embodiments contemplate the method as further comprising the step of tumor resection, after the contacting. In particularly defined embodiments, the cancer is selected from the group consisting of lung, breast, melanoma, colon, renal, testicular, ovarian, lung, prostate, hepatic, germ cancer, epithelial, prostate, head and neck, pancreatic cancer, glioblastoma, astrocytoma, oligodendroglioma, ependymomas, neurofibrosarcoma, meningia, liver, spleen, lymph node, small intestine, blood cells, colon, stomach, thyroid, endometrium, prostate, skin, esophagus, bone marrow and blood.

In other embodiments, the cancer is a solid tumor. In preferred embodiments, the tumor is a sarcoma. In other embodiments, the tumor is an epithelial tumor. In certain embodiments the cancer is a leukemia. In more defined embodiments, the leukemia is a promyelocytic leukemia.

In particular embodiments, the radiation responsive enhancer-promoter comprises at least one distal CArG domain of an Egr-1 promoter, a tumor necrosis factor α promoter or a c-jun promoter. In particular aspects, the CArG domain is from Egr-1 promoter. In other aspects the CArG domain is from tumor necrosis factor α promoter. In still other embodiments, the CArG domain is from c-jun promoter.

In specific embodiments, it is contemplated that the DNA molecule may further comprise a second coding region. The second coding region may encode a gene selected from the group consisting of a tumor suppressor, a cytokine, an enzyme, a receptor, or an inducer of apoptosis. Alternatively, the second coding region comprises an antisense construct. In preferred embodiments, the antisense construct is derived from an oncogene. More particularly, the oncogene may be selected from the group consisting ras, myc, neu, raf erb, src, fms, jun, trk, ret, gsp, hst, bcl and abl. In those embodiment in which the second coding region encodes a tumor suppressor, the tumor suppressor may selected from the group consisting of p53, p16, p21, MMAC1, p73, zac1, BRCAI and Rb. In those embodiment in which the second coding region encodes a tumor cytokine, the cytokine is selected from the group consisting of IL-2, IL-2, IL-3, IL-4, IL-5, IL-6, IL-7, IL-8, IL-9, IL-10, IL-11, IL-12, IL-13, IL-14, IL-15, TNF, GMCSF, β-interferon and γ-interferon. In those embodiments in which the second coding region encodes an enzyme, the enzyme may be selected from the group consisting of cytosine deaminase, adenosine deaminase, β-glucuronidase, hypoxanthine guanine phosphoribosyl transferase, galactose-1-phosphate uridyltransferase, glucocerbrosidase, glucose-6-phosphatase, thymidine kinase and lysosomal glucosidase. In preferred embodiment, the receptor may be selected from the group consisting of CFTR, EGFR, VEGFR, IL-2 receptor and the estrogen receptor. In other embodiment, the inducer of apoptosis is selected from the group consisting of Bax, Bak, Bcl-$X_s$, Bik, Bid, Bad, Harakiri, Ad E1B and an ICE-CED3 protease. In especially preferred embodiments, the subject is a human subject.

The present invention further provides a method of enhancing the effectiveness of ionizing radiotherapy comprising administering, to a tumor site in a mammal, an anti-angiogenic factor protein prior to radiation therapy; and ionizing radiation, wherein the combination of anti-angiogenic factor administration and radiation is more effective than ionizing radiation alone.

In preferred embodiments angiostatin is administered as a protein formulation. In particularly preferred embodiments the angiostatin is delivered as 25 mg angiostatin/kg body weight/day; 30 mg angiostatin/kg body weight/day; 35 mg angiostatin/kg body weight/day; 40 mg angiostatin/kg body weight/day; 50 mg angiostatin/kg body weight/day; 75 mg angiostatin/kg body weight/day; 100 mg angiostatin/kg body weight/day; 150 mg angiostatin/kg body weight/day; 200 mg angiostatin/kg body weight/day; 250 mg angiostatin/kg body weight/day; 300 mg angiostatin/kg body weight/day; 350 mg angiostatin/kg body weight/day; 400 mg angiostatin/kg body weight/day; 450 mg angiostatin/kg body weight/day; 500 mg angiostatin/kg body weight/day; 550 mg angiostatin/kg body weight/day; 600 mg angiostatin/kg body weight/day; 750 mg angiostatin/kg body weight/day; 800 mg angiostatin/kg body weight/day; 900 mg angiostatin/kg body weight/day or 1 g angiostatin/kg body weight/day. Of course, these are only exemplary concentrations and it is well within the skill of one in the art to modify these concentrations to arrive at a dose effective to sensitize cell to radiotherapy as described herein. In other preferred embodiments, the angiostatin is administered as part of a viral expression construct. In certain embodiments, the viral expression construct is in a composition comprising from about $10^8$ to about $10^{10}$ virus particles.

In preferred embodiments endostatin is administered as a protein formulation. In particularly preferred embodiments the endostatin is delivered as 25 mg endostatin/kg body weight/day; 30 mg endostatin/kg body weight/day; 35 mg endostatin/kg body weight/day; 40 mg endostatin/kg body weight/day; 50 mg endostatin/kg body weight/day; 75 mg endostatin/kg body weight/day; 100 mg endostatin/kg body weight/day; 150 mg endostatin/kg body weight/day; 200 mg endostatin/kg body weight/day; 250 mg endostatin/kg body weight/day; 300 mg endostatin/kg body weight/day; 350 mg endostatin/kg body weight/day; 400 mg endostatin/kg body weight/day; 450 mg endostatin/kg body weight/day; 500 mg endostatin/kg body weight/day; 550 mg endostatin/kg body weight/day; 600 mg endostatin/kg body weight/day; 750 mg endostatin/kg body weight/day; 800 mg endostatin/kg body weight/day; 900 mg endostatin/kg body weight/day or 1 g endostatin/kg body weight/day. Of course, these are only exemplary concentrations and it is well within the skill of one in the art to modify these concentrations to arrive at a dose effective to sensitize cell to radiotherapy as described herein. In other preferred embodiments, the endostatin is administered as part of a viral expression construct. In certain embodiments, the viral expression construct is in a composition comprising from about $10^8$ to about $10^{10}$ virus particles.

In still other preferred embodiments IL-12 is administered as a protein formulation. In particularly preferred embodiments the IL-12 is delivered as 0.1 pg IL-12/μg protein/day; 0.5 pg IL-12/μg protein/day; 1.0 pg IL-12/μg protein/day; 5 pg IL-12/μg protein/day; 10 pg IL-12/μg protein/day; 15 pg IL-12/μg protein/day; 20 pg IL-12/μg protein/day; 25 pg IL-12/μg protein/day; 30 pg IL-12/μg protein/day; 35 pg IL-12/μg protein/day; 40 pg IL-12/μg protein/day; 45 pg IL-12/μg protein/day; 50 IL-12/μg protein/day; 55 pg IL-12/μg protein/day; 60 pg IL-12/μg protein/day; 65 pg IL-12/μg protein/day; 75 pg IL-12/μg protein/day; 80 pg IL-12/μg protein/day; 85 pg IL-12/μg protein/day; 90 pg IL-12/μg protein/day; 95 pg IL-12/μg protein/day; 100 pg IL-12/μg protein/day; 200 pg IL-12/μg protein/day; 300 pg IL-12/μg protein/day; 400 pg IL-12/μg protein/day; 500 pg IL-12/μg protein/day; 600 pg IL-12/μg protein/day; 700 pg IL-12/μg protein/day; 800 pg IL-12/μg protein/day; 900 IL-12/μg protein/day; 1,000 pg IL-12/μg protein/day; 2,000 pg L-12/

μg protein/day; 3,000 pg IL-12/μg protein/day; 4,000 pg IL-12/μg protein/day; 5,000 pg IL-12/μg protein/day; 6,000 pg IL-12/μg protein/day; 7,000 pg IL-12/μg protein/day; 8,000 pg IL-12/μg protein/day; 9,000 pg IL-12/μg protein/day or 10,000 pg IL-12/μg protein/day. Of course, these are only exemplary concentrations and it is well within the skill of one in the art to modify these concentrations to arrive at a dose effective to sensitize cell to radiotherapy as described herein. In other preferred embodiments, the IL-12 is administered as part of a viral expression construct. In certain embodiments, the viral expression construct is in a composition comprising from about $10^8$ to about $10^{10}$ virus particles.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A: LLC growth. C57B1/ mice bearing LLC tumors (1104±97.9 mm$^3$) were injected daily for 14 days with human angiostatin and received two 20 Gy doses (days 0 and 1). FIG. 1B: D54 growth. Female nude mice bearing human glioblastoma tumors (385.8±48.2 mm$^3$) were injected with human angiostatin 2 h prior to XRT (5 Gy/day to a total dose of 30 Gy). FIG. 1C: SQ-20B growth (hAS). Athymic nude mice bearing SQ-20B xenografts (675.8±74.7 mm$^3$) received human angiostatin (25 mg/kg/day) 2 h prior to XRT (5 Gy/day, 5 days/week, to 50 Gy). FIG. 1D: SQ-20B growth (mAS). Mice with SQ-20B tumors (535±29.5 mm$^3$) were injected with murine angiostatin (2.5. mg/Kg/day) 2 hours prior to XRT (50 Gy). FIG. 1E: PC3 growth. Mice with PC3 xenografts (769.5±69.5 mm$^3$) were treated with human angiostatin 2 h prior to XRT (5 Gy/day to a total dose of 40 Gy). Combined treatment with angiostatin and XRT produced significant tumor regression in all tumor types (LLC day 9, $p<0.05$; D54 day 21, $p<0.005$; SQ-20B hAS day 21, $p<0.005$; mAS day 21, $p<0.001$; PC3 day 42, $p<0.001$).

FIG. 4A) endothelial cells (200 to 500 HAEC and HUVEC) were plated in EGM2 medium in 100 mm tissue culture dishes. Eighteen h later mouse endostatin (1, 10, 100 or 1000 ng/ml) was added. The dishes were returned to the incubator for 14–17 days after which they were stained with crystal violet, colonies were counted and the surviving fraction was determined. Colonies containing >50 cells were scored as positive. FIG. 4B) endothelial cells (HAEC) were plated in EGM-2 medium. To account for radiation killing, increasing numbers of cells (200 to 10$^4$) were plated in 100 mm tissue culture dishes. Eighteen h after plating endostatin was added at concentrations of 10 and 100 ng/ml. Four h later, cells were irradiated with doses of 100–700 cGy using a GE Maxitron xray generator operating at 26 mA, 250 kV, with a 0.5 mm copper filter, at a dose rate of 118 cGy/min. Cultures were incubated and stained as above.

FIG. 9A) AdIL-12, FIG. 9B) AdIL-12+XRT, FIG. 9C) control, anf FIG. 9D) XRT. (1=smallest third, 2=middle third, 3=largest third).

DESCRIPTION OF ILLUSTRATIVE EMBODIMENTS

Figure 1A:
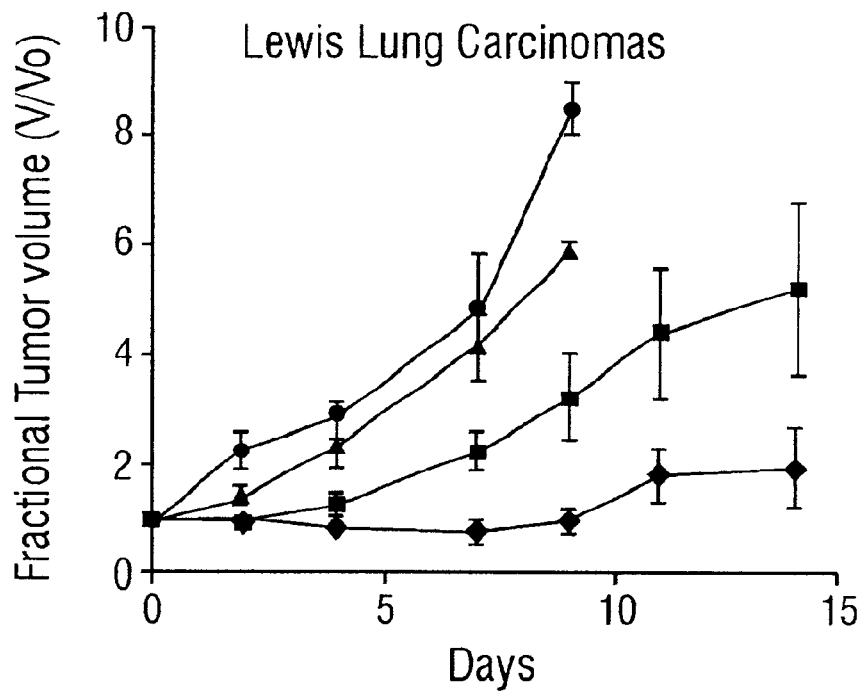
FIG. 1A, FIG. 1B, FIG. 1C, FIG. 1D and FIG. 1E. Tumor growth following combined treatment with angiostatin and I-R.
Figure 1B:
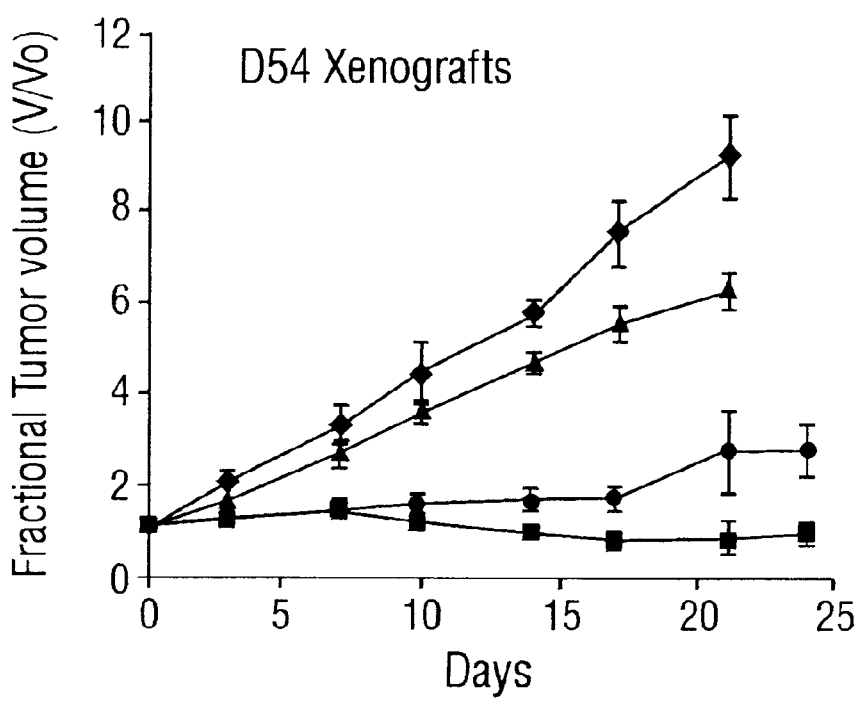
Figure 1C:
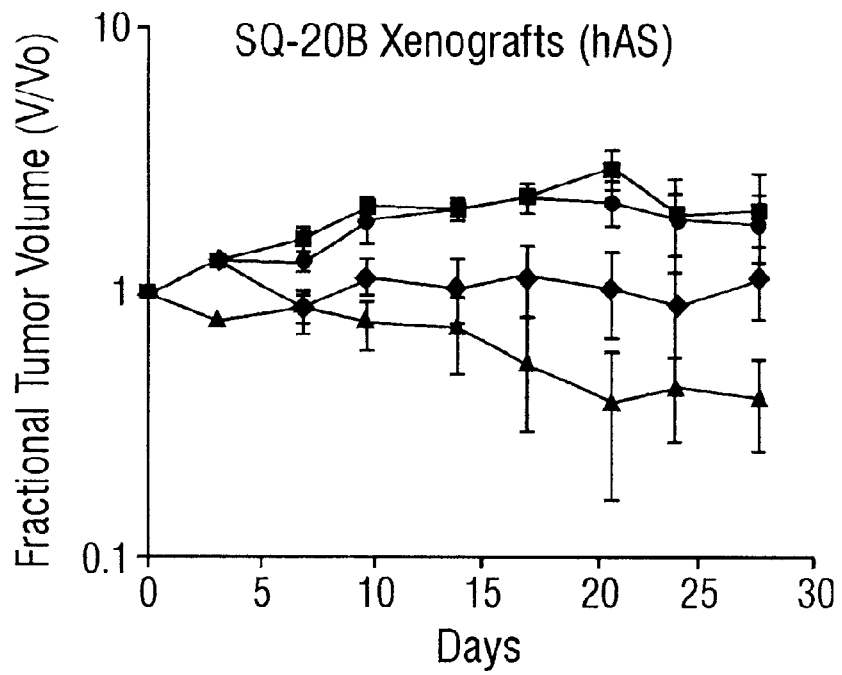
Figure 1D:
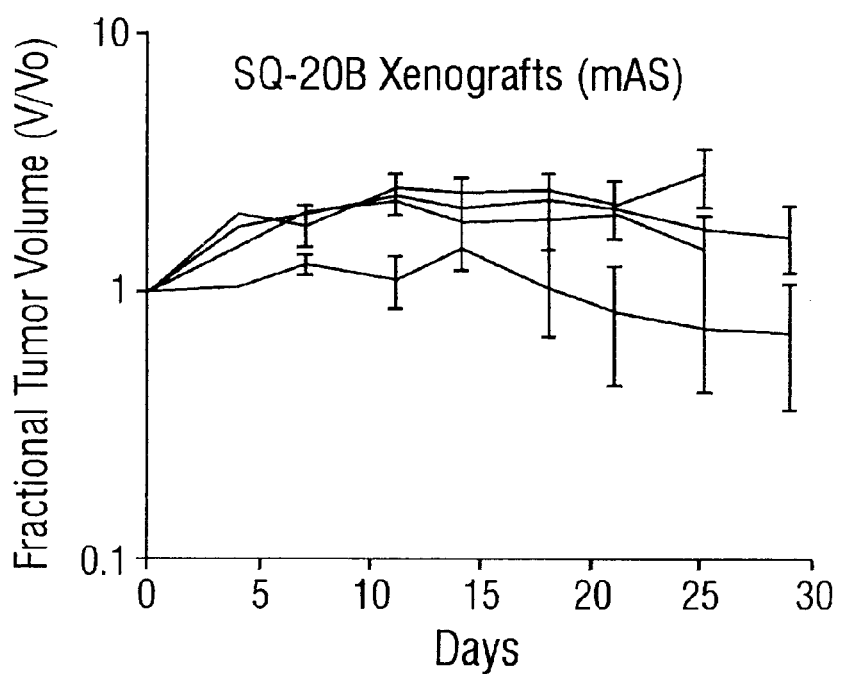
Figure 1E:
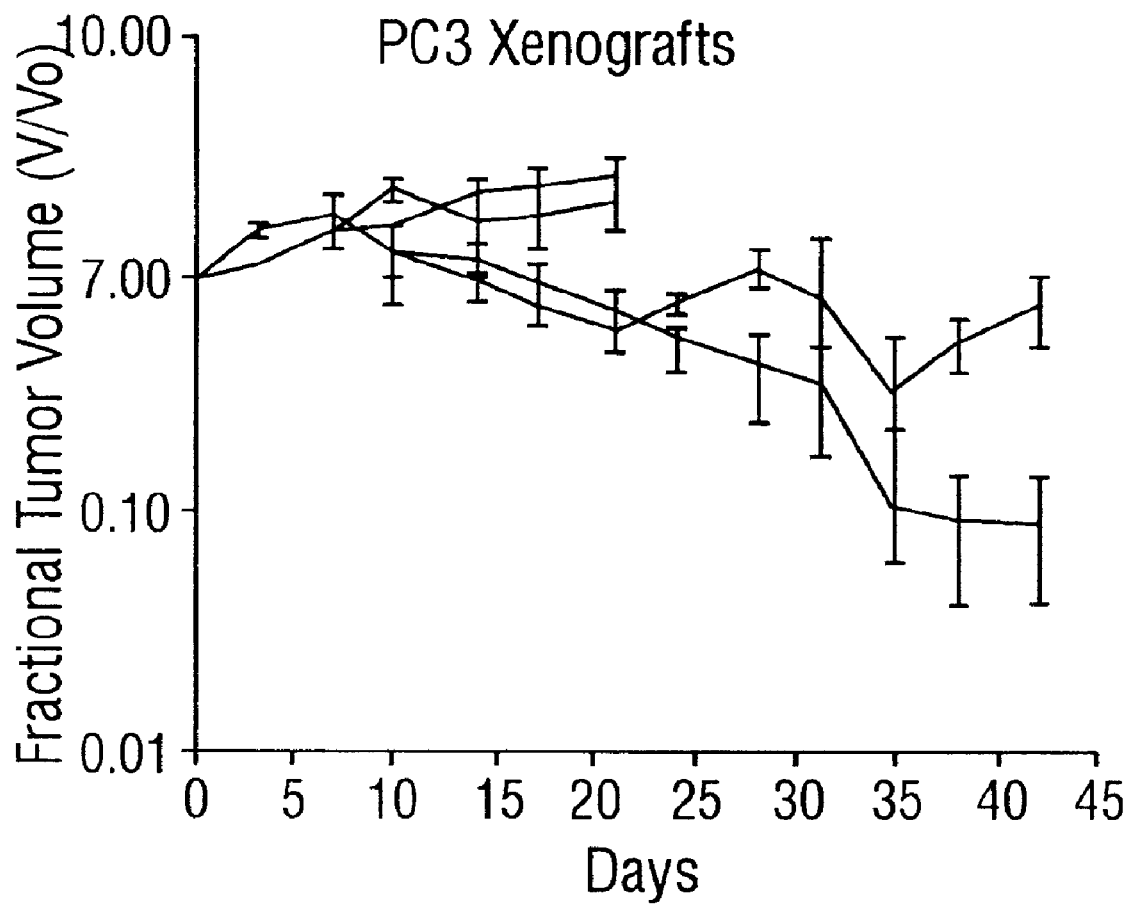

Angiogenesis, the formation of new capillaries from pre-existing vessels, is essential for tumor progression (Folkman and Shing, 1992; Fidler and Ellis, 1994; Folkman, 1995; Hanahan and Folkman, 1996; Rak et al., 1995). Angiostatin, a proteolytic fragment of plasminogen (Cao et al., 1996) first isolated from the serum and urine of tumor bearing mice (O'Reilly et al., 1994), inhibits angiogenesis and thereby growth of primary (O'Reilly et al., 1996) and metastatic tumors (O'Reilly et al., 1994; Holmgren et al., 1995; Sim et al., 1997). Endostatin, a 20 kDa C-terminal proteolytic fragment of collagen XVIII, is an inhibitor of endothelial cell proliferation (Hohenester et al., 1998). Endostatin is produced by hemangioendothelioma and is believed to further inhibit angiogenesis and tumor growth (O'Reilly et al., 1997).

Radiotherapy is an important modality for the treatment of many human cancers, but is often unsuccessful because of tumor cell radioresistance (Weichselbaum et al., 1986; Weichselbaum et al., 1988). Therefore, the inventors combined radiation with anti-angiogenic factors to target the tumor vasculature that is genetically stable and, therefore, less likely to develop resistance (Kerbel, 1991; Kakeji and Teicher, 1997). The present invention demonstrates that the interactive anti-tumor effects of combined treatment with a human anti-angiogenic factor and ionizing radiation (IR) are greater than additive when compared with the expected effects of combined treatment.

The results demonstrate an anti-tumor interaction with ionizing radiation and an anti-angiogenic factor in four distinct tumor types and at doses of radiation that are employed in clinical radiotherapy. Importantly, the combination produced no increase in normal tissue toxicity. In vitro studies demonstrate that irradiation and angiostatin exhibit combined cytotoxic effects on endothelial cells, but not tumor endothelial cells. In vivo studies demonstrate that these agents in combination target the tumor vasculature. The inventors' findings provide support for combining ionizing radiation with an anti-angiogenic factor to improve tumor eradication without increasing deleterious effects. Methods and compositions for achieving these objectives are described in detail herein below.

A. Angiostatin

Angiostatin is a protein having a molecular weight of between approximately 38 kilodaltons and 45 kilodaltons as determined by reducing polyacrylamide gel electrophoresis. Angiostatin inhibits the growth of blood vessels into tissues such as vascularized tumors and is capable of overcoming the angiogenic activity of endogenous growth factors such as βFGF, in vitro.

The angiostatin used herein can be isolated from body fluids including, but not limited to, serum, urine and ascites, or synthesized by chemical or biological methods (e.g. cell culture, recombinant gene expression, and in vitro enzymatic catalysis of plasminogen or plasmin to yield active angiostatin). Recombinant techniques include gene amplification from DNA sources using the polymerase chain reaction (PCR), and gene amplification from RNA sources using reverse transcriptase/PCR.

Methods and compositions comprising angiostatin and uses thereof are described in U.S. Pat. No. 5,639,725, (specifically incorporated herein by reference). U.S. Pat. No. 5,733,876 (specifically incorporated herein by reference) describes methods for inhibiting angiogenesis comprising administering to a mammal an effective amount of angiostatin protein. In this referenced document the angiostatin protein contains approximately kringle regions 1 through 4 of a plasminogen molecule and has anti-angiogenic activity. Additional information regarding angiostatin and methods of use thereof include WO 96/35774 and WO 95/29242, each incorporated herein by reference.

The present invention provides methods and compositions for treating a human or other animal having a cell that is insensitive to radiotherapy by administering to said human or animal, a composition comprising an angiostatin or angiostatin derivative in a dosage sufficient to sensitize the cell of said animal to a dose of radiotherapy. Of course the angiostatin may be administered to further inhibit angiogenesis. The present invention is particularly useful for treating or for repressing the growth of tumors by first delivering a dose of angiostatin effective to sensitize the tumor to a dose of radiation and then exposing the cell to radiotherapy in an amount effective to inhibit, repress, abrogate or otherwise diminish the growth of the tumor. Administration of angiostatin followed by radiotherapy, as described herein, to a human or animal with prevascularized metastasized tumors will prevent the growth or expansion of those tumors. Accordingly, it is an object of the present invention to provide a composition comprising an angiostatin protein followed by a dose of radiotherapy. It is further object of the present invention to provide a method for treating or repressing the growth of a cancer.

As stated earlier, the angiostatin can be isolated from a body fluid such as blood or urine of patients or the angiostatin can be produced by recombinant DNA methods or synthetic peptide chemical methods that are well known to those of ordinary skill in the art. Protein purification methods are well known in the art and are discuss ed in further detail herein below. Isolation of human endogenous angiostatin is accomplished using similar techniques. The gene for angiostatin may also be isolated from cells or tissue (such as tumor endothelial cells ) that express high levels of angiostatin by isolating messenger RNA from the tissue, using reverse transcriptase to generate the corresponding DNA sequence and then using PCR with the appropriate primers to amplify the DNA sequence coding for the active angiostatin amino acid sequence (Sambrook et aL, 1989).

Yet another method of producing angiostatin, or biologically active fragments thereof, is by peptide synthesis. Once a biologically active fragment of an angiostatin is found e.g. as described in U.S. Pat. No. 5,733,876, it can be sequenced, for example by automated peptide sequencing methods. Alternatively, once the gene or DNA sequence which codes for angiostatin is isolated, for example by the methods U.S. Pat. No. 5,733,876, the DNA sequence c an be determined, which in turn provides information regarding the amino acid sequence. Thus, if the biologically active fragment is generated by specific methods, such as tryptic digests, or if the fragment is N-terminal sequenced, the remaining amino acid sequence can be determined from the corresponding DNA sequence. Such methods of making and purifying angiostatin are described in detail herein below.

B. Endostatin Endostatin is a C-terminal proteolytic fragment of collagen XVIII having a molecular weight of approximately 20 kDa (Hohenester et al., 1998). Endostatin, produced by hemangioendothelioma, is an inhibitor of endothelial proliferation and is believed to inhibit angiogenesis and tumor growth (O'Reilly et al., 1997). A putative mechanism of endostatin inhibition of angiogenesis has been derived from the 1.5 Å endostatin crystal structure (Hohenester et al., 1998). The endostatin structure reveals a compact fold distantly related to the C-type lectin carbohydrate recognition domain, the hyaluronan-binding Link module, and an extensive basic patch formed by 11 arginine residues. It was conjectured that basic patch on endostatin confers its high affinity for heparin and that endostatin may inhibit angiogenesis by binding heparin sulfate proteoglycans involved in growth factor signaling.

Endostatin can be isolated from murine hemangioendothelioma EOMA (U.S. Pat. No. 5,854,205, specifically incorporated herein by reference in its entirety). Endostatin may be produced from recombinant sources, from genetically altered cells implanted into animals, from tumors, and from cell cultures as well as other sources. It is anticipated that endostatin is made in cells of the nervous system. Endostatin can be isolated from body fluids including, but not limited to, serum, urine and ascites, or synthesized by chemical or biological methods (e.g. cell culture, recombinant gene expression, peptide synthesis, and in vitro enzymatic catalysis of precursor molecules to yield active endostatin).

Recombinant techniques include gene amplification from DNA sources using the polymerase chain reaction (PCR), and gene amplification from RNA sources using reverse transcriptase/PCR. Endostatin specifically and reversibly inhibits endothelial cell proliferation. The inhibitor protein molecules are useful as for treating angiogenesis-related diseases, particularly angiogenesis-dependent cancers and tumors. Endostatin proteins of the present invention can be made by automated protein synthesis methodologies well known to one skilled in the art. Alternatively, endostatins, of the present invention may be isolated from larger known proteins, such as human alpha 1 type XVIII collagen and mouse alpha 1 type XVIII collagen, proteins that share a common or similar N-terminal amino acid sequence, as described in U.S. Pat. No. 5,854,205. Examples of other potential endostatin source materials having similar N-terminal amino acid sequences include Bos taurus pregastric esterase, human alpha 1 type 15 collagen, NAD-dependent formate dehydrogenase (EC 1.2.1.2) derived from Pseudomonas sp., s11459 hexon protein of bovine adenovirus type 3, CELF-21D12 2F21d12.3 Caenorhabditis elegans gene product VAL1 TGMV AL1 protein derived from tomato golden mosaic virus, s01730 hexon protein derived from human adenovirus 12, Saccharomyces cerevisiae. For example, peptides closely related to endostatin may be derived from BOVMPE 1 pregastric esterase (BOS TAURUS) gene sequence corresponding to amino acids 502 to 521, and collagen alpha 1 type 15 from humans beginning at amino acid 316 ending at 335.

Endostatin is effective in treating diseases or processes that are mediated by, or involve, angiogenesis. The present invention provides methods and compositions for treating a human or other animal having a cell that is insensitive to radiotherapy by administering to said human or animal, a composition comprising an endostatin or an endostatin derivative in a dosage sufficient to sensitize the cell of said animal to a dose of radiotherapy. Of course the endostatin may be administered to further inhibit angiogenesis. The present invention is particularly useful for treating or for repressing the growth of tumors by first delivering a dose of anti-angiogenic factor effective to sensitize the tumor to a dose of radiation and then exposing the cell to radiotherapy in an amount effective to inhibit, repress, abrogate or otherwise diminish the growth of the tumor. Administration of anti-angiogenic factor followed by radiotherapy, as described herein, to a human or animal with prevascularized metastasized tumors will prevent the growth or expansion of those tumors. Accordingly, it is an object of the present invention to provide a composition comprising an anti-angiogenic factor protein followed by a dose of radiotherapy. It is further object of the present invention to provide a method for treating or repressing the growth of a cancer.

C. IL-12

Immunization against putative tumor associated antigens is an emerging strategy in clinical oncology. One method of immunization is local intratumoral delivery of genes encoding cytokines or costimulatory molecules to induce specific antitumor immunity and circumvent systemic toxicity. In one embodiment of the present invention, there is provided a method of inhibiting cancer growth by administering IL-12 in combination with an anti-angiogenic factor. More particularly, the method may involve administering a DNA molecule encoding IL-12. The DNA molecule will of course comprise the IL-12 coding region and other regulatory elements such as promoters, enhancers and the like. The anti-angiogenic factor and IL-12 may be administered as a single expression construct, wherein the expression construct comprises a polynucleotide having an anti-angiogenic factor coding region and an IL-12 coding region, or alternatively the anti-angiogenic factor may be administered as a second expression construct. It is further contemplated that the IL-12 and anti-angiogenic factor may be administered alone or in combination as protein formulations. Subsequent to IL-12 induced antitumor immunity, the cancer cells are exposed to a dose of ionizing radiation, a combinational approach considered to be effective in both local and distant tumor growth.

IL-12 is a heterodimeric cytokine that is produced primarily by antigen presenting cells (APCs) and plays an important role in mediating immune responses. Mechanisms of action of IL-12 includes stimulation of CD4, CD8 and natural killer cells. IL-12 also increases production of IFNγ by natural killer and T cells. Studies in animals and the results of human clinical trials suggest that IL-12 - activated CD8+T cells play a crucial role in antitumor immunity. However, human trials administering IL-12 alone as an antitumor agent have to date been unsuccessful. Thus, it is contemplated in the present invention, that IL-12 might enhance the local antitumor effects of ionizing radiation as a consequence of anti-angiogenic effects and suppress tumors distant from the primary site by priming the immune system. Also considered is a new role for the combination radiotherapy and IL-12 immunotherapy in the treatment of locally radioresistant human cancers and a useful adjuvant treatment for metastases.

D. Engineering Expression Constructs

In particular embodiments, it may be necessary to make recombinant anti-angiogenic factor, alternatively, the anti-angiogenic factor used for therapeutic applications may be presented as an anti-angiogenic factor gene in an expression construct for anti-angiogenic factor based gene therapy. These embodiments involve the manipulation of genetic material to produce expression constructs that encode anti-angiogenic factor. Such methods involve the generation of expression constructs containing, for example, a heterologous DNA encoding a gene and a means for its expression, replicating the vector in an appropriate helper cell, obtaining viral particles produced therefrom, and infecting cells with the recombinant virus particles. Additionally, the anti-angiogenic factor/radiotherapy modality for cancer treatment presented herein may be combined with other therapeutic genes used in cancer therapy. The following discussion is directed toward engineering expression constructs for recombinant protein production and/or gene therapy.

The gene will be a therapeutic gene that encodes an anti-angiogenic factor protein, or the gene may be a second therapeutic gene or nucleic acid useful in the treatment of, for example, cancer cells. In the context of gene therapy, the gene will be a heterologous DNA, meant to include DNA derived from a source other than the viral genome which provides the backbone of the vector. Finally, the virus may act as a live viral vaccine and express an antigen of interest for the production of antibodies thereagainst. The gene may be derived from a prokaryotic or eukaryotic source such as a bacterium, a virus, a yeast, a parasite, a plant, or even an animal. The heterologous DNA also may be derived from more than one source, i.e., a multigene construct or a fusion protein. The heterologous DNA also may include a regulatory sequence which may be derived from one source and the gene from a different source.

i. Additional Therapeutic Genes

The present invention contemplates the use of a variety of different genes in combination with anti-angiogenic factor constructs. For example, genes encoding enzymes, hormones, cytokines, oncogenes, receptors, tumor suppressors, transcription factors, drug selectable markers, toxins and various antigens are contemplated as suitable genes for use according to the present invention. In addition, antisense constructs derived from oncogenes are other "genes" of interest according to the present invention.

a. Tumor Suppressors p53. p53 currently is recognized as a tumor suppressor gene. High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently-mutated gene in common human cancers. It is mutated in over 50% of human NSCLC (Hollstein et al., 1991) and in a wide spectrum of other tumors.

Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

p53 appears dominant over the mutant gene and will select against proliferation when transfected into cells with the mutant gene. Normal expression of the transfected p53 does not affect the growth of cells with endogenous p53. Thus, such constructs might be taken up by normal cells without adverse effects. It is thus proposed that the treatment of p53-associated cancers with wild-type p53 or other therapies described herein will reduce the number of malignant cells or their growth rate, alternatively the treatment will result in the decrease of the metastatic potential of the cancer cell, a decrease in tumor size or a halt in the growth the tumor.

p16. The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit, the $p16^{INK4}$ has been biochemically characterized as a protein that specifically binds to and inhibits CDK4, and thus may regulate Rb phosphorylation (Serrano et al., 1993; Serrano et al., 1995). Since the $p_{16}^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

C-CAM is expressed in virtually all epithelial cells (Odin and Obrink, 1987). C-CAM, with an apparent molecular weight of 105 kDa, was originally isolated from the plasma membrane of the rat hepatocyte by its reaction with specific antibodies that neutralize cell aggregation (Obrink, 1991). Recent studies indicate that, structurally, C-CAM belongs to the immunoglobulin (Ig) superfamily and its sequence is highly homologous to carcinoembryonic antigen (CEA) (Lin and Guidotti, 1989). Using a baculovirus expression system, Cheung et al. (1993) demonstrated that the first Ig domain of C-CAM is critical for cell adhesive activity.

Cell adhesion molecules, or CAM's are known to be involved in a complex network of molecular interactions that regulate organ development and cell differentiation (Edelman, 1985). Recent data indicate that aberrant expression of CAM's maybe involved in the tumorigenesis of several neoplasms; for example, decreased expression of E-cadherin, which is predominantly expressed in epithelial cells, is associated with the progression of several kinds of neoplasms (Edelman and Crossin, 1991; Frixen et al., 1991; Bussemakers et al., 1992; Matsura et al., 1992; Umbas et al., 1992). Also, Giancotti and Ruoslahti (1990) demonstrated that increasing expression of $\alpha_5\beta_1$ integrin by gene transfer can reduce tumorigenicity of Chinese hamster ovary cells in vivo. C-CAM now has been shown to suppress tumors growth in vitro and in vivo.

Additional Tumor Suppressors. Other tumor suppressors that may be employed according to the present invention include RB, APC, DCC, NF-1, NF-2, WT-1, MEN-I, MEN-II, zac1, p73, VHL, MMAC1, FCC and MCC. Additional inducers of apoptosis including members of the Bcl-2 family such as Bax, Bak, Bim, Bik, Bid, or Bad gene, as well as Ad E1B and ICE-CED3 proteases, similarly could find use according to the present invention.

b. enzymes

Various enzyme genes are of interest according to the present invention. Such enzymes include cytosine deaminase, hypoxanthine-guanine phosphoribosyltransferase, galactose-1-phosphate uridyltransferase, phenylalanine hydroxylase, glucocerbrosidase, sphingomyelinase, $\alpha$-L-iduronidase, glucose-6-phosphate dehydrogenase, HSV thymidine kinase and human thymidine kinase.

C. Cytokines

Other classes of genes that are contemplated to be inserted into the therapeutic expression constructs of the present invention include interleukins and cytokines. Interleukin 1 (IL-1), IL-2, IL-3, IL-4, IL-5, IL-6, IL-7, IL-8, IL-9, IL-10, IL-11 IL-12, GM-CSF and G-CSF.

d. antibodies

In yet another embodiment, the heterologous gene may include a single-chain antibody. Methods for the production of single-chain antibodies are well known to those of skill in the art. The skilled artisan is referred to U.S. Pat. No. 5,359,046, (incorporated herein by reference) for such methods. A single chain antibody is created by fusing together the variable domains of the heavy and light chains using a short peptide linker, thereby reconstituting an antigen binding site on a single molecule.

Single-chain antibody variable fragments (Fvs) in which the C-terminus of one variable domain is tethered to the N-terminus of the other via a 15 to 25 amino acid peptide or linker, have been developed without significantly disrupting antigen binding or specificity of the binding (Bedzyk et al., 1990; Chaudhary et al., 1990). These Fvs lack the constant regions (Fc) present in the heavy and light chains of the native antibody.

Antibodies to a wide variety of molecules can be used in combination with the present invention, including antibodies against oncogenes, toxins, hormones, enzymes, viral or bacterial antigens, transcription factors, receptors and the like.

For example, several factors have been described that might act as regulators of angiogenesis (Klagsbrun and D'Amore, 1991). These include transforming growth factor (TGFb), acidic and basic fibroblast growth factor (aFGF and bFGF), platelet derived growth factor (PDGF), and vascular endothelial growth factor (VEGF). VEGF, an endothelial cell-specific mitogen, is distinct among these factors in that it acts as an angiogenesis inducer by specifically promoting the proliferation of endothelial cells. It is contemplated in one embodiment of the present invention, that an antibody against vascular endothelial growth factor (VEGF) is provided in addition to an anti-angiogenic factor, to further inhibit angiogenesis (U.S. Pat. Nos. 5,874,542, 5,733,876, 5,859,018, 5,801,156, 5,861,484, each specifically incorporated herein by reference).

ii. Antisense constructs

Oncogenes such as ras, myc, neu, raf, erb, src, fins, jun, trk, ret, gsp, hst, bcl-2, BCl-$x_L$ and abl also are suitable targets. However, for therapeutic benefit, these oncogenes would be expressed as an antisense nucleic acid, so as to inhibit the expression of the oncogene. The term "antisense nucleic acid" is intended to refer to the oligonucleotides complementary to the base sequences of oncogene-encoding DNA and RNA. Antisense oligonucleotides, when introduced into a target cell, specifically bind to their target nucleic acid and interfere with transcription, RNA processing, transport and/or translation. Targeting double-stranded (ds) DNA with oligonucleotide leads to triple-helix formation; targeting RNA will lead to double-helix formation.

Antisense constructs may be designed to bind to the promoter and other control regions, exons, introns or even exon-intron boundaries of a gene. Antisense RNA constructs, or DNA encoding such antisense RNAs, may be employed to inhibit gene transcription or translation or both within a host cell, either in vitro or in vivo, such as within a host animal, including a human subject. Nucleic acid sequences comprising "complementary nucleotides" are those which are capable of base-pairing according to the standard Watson-Crick complementary rules. That is, that the larger purines will base pair with the smaller pyrimidines to form only combinations of guanine paired with cytosine (G:C) and adenine paired with either thymine (A:T), in the case of DNA, or adenine paired with uracil (A:U) in the case of RNA.

As used herein, the terms "complementary" or "antisense sequences" mean nucleic acid sequences that are substantially complementary over their entire length and have very few base mismatches. For example, nucleic acid sequences of fifteen bases in length may be termed complementary when they have a complementary nucleotide at thirteen or fourteen positions with only single or double mismatches. Naturally, nucleic acid sequences which are "completely complementary" will be nucleic acid sequences which are entirely complementary throughout their entire length and have no base mismatches.

While all or part of the gene sequence may be employed in the context of antisense construction, statistically, any sequence 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that oligonucleotides of 8, 9, 10, 11, 12, 13, 14, 15, 16, 17, 18, 19, 20 or more base pairs will be used. One can readily determine whether a given antisense nucleic acid is effective at targeting of the corresponding host cell gene simply by testing the constructs in vitro to determine whether the endogenous gene's function is affected or whether the expression of related genes having complementary sequences is affected.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

iii. Ribozyme constructs

As an alternative to targeted antisense delivery, targeted ribozymes may be used. The term "ribozyme" refers to an RNA-based enzyme capable of targeting and cleaving particular base sequences in oncogene DNA and RNA. Ribozymes either can be targeted directly to cells, in the form of RNA oligo-nucleotides incorporating ribozyme sequences, or introduced into the cell as an expression construct encoding the desired ribozymal RNA. Ribozymes may be used and applied in much the same way as described for antisense nucleic acids.

iv. Selectable Markers

In certain embodiments of the invention, the therapeutic expression constructs of the present invention contain nucleic acid constructs whose expression may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants. For example, genes that confer resistance to neomycin, puromycin, hygromycin, DHFR, GPT, zeocin and histidinol are useful selectable markers. Alternatively, enzymes such as herpes simplex virus thymidine kinase (tk) may be employed. Immunologic markers also can be employed. The selectable marker employed is not believed to be important, so long as it is capable of being expressed simultaneously with the nucleic acid encoding a gene product. Further examples of selectable markers are well known to one of skill in the art and include reporters such as EGFP, β-gal or chloramphenicol acetyltransferase (CAT).

V. Multigene Constructs and IRES

In certain embodiments of the invention, the use of internal ribosome binding sites (IRES) elements are used to create multigene polycistronic messages. IRES elements are able to bypass the ribosome scanning model of 5'-methylated, Cap-dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

vi. Control Regions

A. Promoters

Throughout this application, the term "expression construct" is meant to include any type of genetic construct containing a nucleic acid coding for gene products in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding genes of interest.

The nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, β-actin, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it may be desirable to prohibit or reduce expression of one or more of the transgenes. Examples of transgenes that may be toxic to the producer cell line are pro-apoptotic and cytokine genes. Several inducible promoter systems are available for production of viral vectors where the transgene product may be toxic.

The ecdysone system (Invitrogen, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. The system is based on the heterodimeric ecdysone receptor of Drosophila, and when ecdysone or an analog such as muristerone A binds to the receptor, the receptor activates a promoter to turn on expression of the downstream transgene high levels of mRNA transcripts are attained. In this system, both monomers of the heterodimeric receptor are constituitively expressed from one vector, whereas the ecdysone-responsive promoter which drives expression of the gene of interest is on another plasmid. Engineering of this type of system into the gene transfer vector of interest would therefore be useful. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristeron A.

Another inducible system that would be useful is the Tet-Off™ or Tet-On™ system (Clontech, Palo Alto, Calif.) originally developed by Gossen and Bujard (Gossen and Bujard, 1992; Gossen et al., 1995). This system also allows high levels of gene expression to be regulated in response to tetracycline or tetracycline derivatives such as doxycycline. i the Tet-On™ system, gene expression is turned on in the presence of doxycycline, whereas in the Tet-Off™ system, gene expression is turned on in the absence of doxycycline. These systems are based on two regulatory elements derived from the tetracycline resistance operon of E. coli. The tetracycline operator sequence to which the tetracycline repressor binds, and the tetracycline repressor protein. The gene of interest is cloned into a plasmid behind a promoter that has tetracycline-responsive elements present in it. A second plasmid contains a regulatory element called the tetracycline-controlled transactivator, which is composed, in the Tet-Off™ system, of the VP16 domain from the herpes simplex virus and the wild-type tertracycline repressor. Thus in the absence of doxycycline, transcription is constituitively on. In the Tet-On™ system, the tetracycline repressor is not wild type and in the presence of doxycycline activates transcription. For gene therapy vector production, the Tet-Off™ system would be preferable so that the producer cells could be grown in the presence of tetracycline or doxycycline and prevent expression of a potentially toxic transgene, but when the vector is introduced to the patient, the gene expression would be constituitively on.

In some circumstances, it may be desirable to regulate expression of a transgene in a gene therapy vector. For example, different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoetic cells is desired, retroviral promoters such as the LTRs from MLV or MMTV are often used. Other viral promoters that may be used depending on the desired effect include SV40, RSV LTR, HIV-1 and HIV-2 LTR, adenovirus promoters such as from the E1A, E2A, or MLP region, AAV LTR, cauliflower mosaic virus, HSV-TK, and avian sarcoma virus.

Similarly tissue specific promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate. Similarly, the following promoters may be used to target gene expression in other tissues (Table 1).

TABLE 1

Tissue specific promoters

| Tissue | Promoter |
|---|---|
| Pancreas | insulin |
| | elastin |
| | amylase |
| | pdr-1 pdx-1 |
| | glucokinase |
| Liver | albumin PEPCK |
| | HBV enhancer |
| | alpha fetoprotein |
| | apolipoprotein C |
| | alpha-1 antitrypsin |
| | vitellogenin, NF-AB |
| | Transthyretin |
| Skeletal muscle | myosin H chain |
| | muscle creatine kinase |
| | dystrophin |
| | calpain p94 |
| | skeletal alpha-actin |
| | fast troponin 1 |
| Skin | keratin K6 |
| | keratin K1 |
| Lung | CFTR |
| | human cytokeratin 18 (K18) |
| | pulmonary surfactant proteins A, B and C |
| | CC-10 |
| | P1 |
| Smooth muscle | sm22 alpha |
| | SM-alpha-actin |
| Endothelium | endothelin-1 |
| | E-selectin |
| | von Willebrand factor |
| | TIE (Korhonen et al., 1995) |
| | KDR/flk-1 |
| Melanocytes | tyrosinase |
| Adipose tissue | lipoprotein lipase (Zechner et al., 1988) |
| | adipsin (Spiegelman et al., 1989) |
| | acetyl-COA carboxylase (Pape and Kim, 1989) |
| | glycerophosphate dehydrogenase (Dani et al., 1989) |
| | adipocyte P2 (Hunt et al., 1986) |
| Blood | β-globin |

In certain indications, it may be desirable to activate transcription at specific times after administration of the gene therapy vector. This may be done with such promoters as those that are hormone or cytokine regulatable. For example in gene therapy applications where the indication is a gonadal tissue where specific steroids are produced or routed to, use of androgen or estrogen regulated promoters may be advantageous. Such promoters that are hormone regulatable include MMTV, MT-1, ecdysone and RuBisco. Other hormone regulated promoters such as those responsive to thyroid, pituitary and adrenal hormones are expected to be useful in the present invention. Cytokine and inflammatory protein responsive promoters that could be used include K and T Kininogen (Kageyama et al., 1987), c-fos, TNF-alpha, C-reactive protein (Arcone et al., 1988), haptoglobin (Oliviero et al., 1987), serum amyloid A2, C/EBP alpha, IL-1, IL-6 (Poli and Cortese, 1989), Complement C3 (Wilson et al., 1990), IL-8, alpha-1 acid glycoprotein (Prowse and Baumann, 1988), alpha-1 antitrypsin, lipoprotein lipase (Zechner et al., 1988), angiotensinogen (Ron et al., 1991), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 antichymotrypsin.

It is envisioned that cell cycle regulatable promoters may be useful in the present invention. For example, in a bi-cistronic gene therapy vector, use of a strong CMV promoter to drive expression of a first gene such as p16 that arrests cells in the G1 phase could be followed by expression of a second gene such as p53 under the control of a promoter that is active in the G1 phase of the cell cycle, thus providing a "second hit" that would push the cell into apoptosis. Other promoters such as those of various cyclins, PCNA, galectin-3, E2F1, p53 and BRCAI could be used.

Tumor specific promoters such as osteocalcin, hypoxia-responsive element (HRE), MAGE-4, CEA, alpha-fetoprotein, GRP78/BiP and tyrosinase may also be used to regulate gene expression in tumor endothelial cells. Other promoters that could be used according to the present invention include Lac-regulatable, chemotherapy inducible (e.g. MDR), and heat (hyperthermia) inducible promoters, Radiation-inducible (e.g., EGR (Joki et al., 1995)), Alpha-inhibin, RNA pol III tRNA met and other amino acid promoters, U1 snRNA (Bartlett et al., 1996), MC-1, PGK, -actin and alpha-globin. Many other promoters that may be useful are listed in Walther and Stein (1996).

It is envisioned that any of the above promoters alone or in combination with another may be useful according to the present invention depending on the action desired. In addition, this list of promoters is should not be construed to be exhaustive or limiting, those of skill in the art will know of other promoters that may be used in conjunction with the promoters and methods disclosed herein.

B. Enhancers

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of promoters additional to the tissue specific promoters listed above, cellular promoters/ enhancers and inducible promoters/enhancers that could be used in combination with the nucleic acid encoding a gene of interest in an expression construct (Table 2 and Table 3). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 2

ENHANCER

Immunoglobulin Heavy Chain
Immunoglobulin Light Chain
T-Cell Receptor
HLA DQ α and DQ β
β-Interferon
Interleukin-2
Interleukin-2 Receptor
MHC Class II 5
MHC Class II HLA-DRα
β-Actin
Muscle Creatine Kinase
Prealbumin (Transthyretin)
Elastase I
Metallothionein
Collagenase
Albumin Gene
α-Fetoprotein
τ-Globin
β-Globin
e-fos
c-HA-ras
Insulin
Neural Cell Adhesion Molecule (NCAM)
α1 -Antitrypsin
H2B (TH2B) Histone
Mouse or Type I Collagen
Glucose-Regulated Proteins (GRP94 and GRP78)
Rat Growth Hormone
Human Serum Amyloid A (SAA)
Troponin I (TN I)
Platelet-Derived Growth Factor
Duchenne Muscular Dystrophy
SV40
Polyoma
Retroviruses
Papilloma Virus
Hepatitis B Virus
Human Immunodeficiency Virus
Cytomegalovirus
Gibbon Ape Leukemia Virus

TABLE 3

| Element | Inducer |
| --- | --- |
| MT II | Phorbol Ester (TPA) |
|  | Heavy metals |
| MMTV (mouse mammary tumor virus) | Glucocorticoids |
| β-Interferon | poly(rI)X |
|  | poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |

TABLE 3-continued

| Element | Inducer |
| --- | --- |
| Proliferin | Phorbol Ester-TPA |
| Tumor Necrosis Factor | FMA |
| Thyroid Stimulating Hormone α Gene | Thyroid Hormone |
| Insulin E Box | Glucose |

In preferred embodiments of the invention, the expression construct comprises a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

C. Polyadenylation Signals

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human or bovine growth hormone and SV40 polyadenylation signals. Also contemplated as an element of the expression cassette is a terminator. These elements can serve to enhance message levels and to minimize read through from the cassette into other sequences.

E. Protein Purification

Certain aspects of the present invention concern the purification, and in particular embodiments, the substantial purification, of the anti-angiogenic factor protein that is encoded by the expression constructs described herein above. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50% or more of the proteins in the composition.

Various methods for quantifying the degree of purification of the protein or peptide will be known to those of skill in the art in light of the present disclosure. These include, for example, determining the specific activity of an active fraction, or assessing the number of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater-fold purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary. Angiostatin is a protein having a molecular weight of between approximately 38 kilodaltons and 45 kilodaltons as determined by reducing polyacrylamide gel electrophoresis (U.S. Pat. No. 5,733,876, specifically incorporated herein by reference).

High Performance Liquid Chromatography (HPLC) is characterized by a very rapid separation with extraordinary resolution of peaks. This is achieved by the use of very fine particles and high pressure to maintain and adequate flow rate. Separation can be accomplished in a matter of minutes, or a most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

F. Methods of Gene Transfer

In order to mediate the effect transgene expression in a cell, it will be necessary to transfer the therapeutic expression constructs of the present invention into a cell. Such transfer may employ viral or non-viral methods of gene transfer. This section provides a discussion of methods and compositions of gene transfer.

i. Viral Vector-Mediated Transfer

The therapeutic genes are incorporated into a viral infectious particle to mediate gene transfer to a cell. Additional expression constructs encoding other therapeutic agents as described herein may also be transferred via viral transduction using infectious viral particles, for example, by transformation with an adenovirus vector of the present invention as described herein below. Alternatively, retroviral or bovine papilloma virus may be employed, both of which permit permanent transformation of a host cell with a gene(s) of interest. Thus, in one example, viral infection of cells is used in order to deliver therapeutically significant genes to a cell. Typically, the virus simply will be exposed to the appropriate host cell under physiologic conditions, permitting uptake of the virus. The present methods may be advantageously employed using a number of viral vectors, as discussed below.

Adenovirus. Adenovirus is particularly suitable for use as a gene transfer vector because of its mid-sized DNA genome, ease of manipulation, high titer, wide target-cell range, and high infectivity. The roughly 36 kB viral genome is bounded by 100–200 base pair (bp) inverted terminal repeats (ITR), in which are contained cis-acting elements necessary for viral DNA replication and packaging. The early (E) and late (L) regions of the genome that contain different transcription units are divided by the onset of viral DNA replication.

The El region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence which makes them preferred mRNAs for translation.

In order for adenovirus to be optimized for gene therapy, it is necessary to maximize the carrying capacity so that large segments of DNA can be included. It also is very desirable to reduce the toxicity and immunologic reaction associated with certain adenoviral products. The two goals are, to an extent, coterminous in that elimination of adenoviral genes serves both ends. By practice of the present invention, it is possible achieve both these goals while retaining the ability to manipulate the therapeutic constructs with relative ease.

The large displacement of DNA is possible because the cis elements required for viral DNA replication all are localized in the inverted terminal repeats (ITR) (100–200 bp) at either end of the linear viral genome. Plasmids containing ITR's can replicate in the presence of a non-defective adenovirus (Hay et al., 1984). Therefore, inclusion of these elements in an adenoviral vector should permit replication.

In addition, the packaging signal for viral encapsidation is localized between 194–385 bp (0.5–1.1 map units) at the left end of the viral genome (Hearing et al., 1987). This signal mimics the protein recognition site in bacteriophage λ DNA where a specific sequence close to the left end, but outside the cohesive end sequence, mediates the binding to proteins that are required for insertion of the DNA into the head structure. E1 substitution vectors of Ad have demonstrated that a 450 bp (0–1.25 map units) fragment at the left end of the viral genome could direct packaging in 293 cells (Levrero et al., 1991).

Previously, it has been shown that certain regions of the adenoviral genome can be incorporated into the genome of mammalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants.

Replication-deficient adenoviral vectors can be complemented, in trans, by helper virus. This observation alone does not permit isolation of the replication-deficient vectors, however, since the presence of helper virus, needed to provide replicative functions, would contaminate any preparation. Thus, an additional element was needed that would add specificity to the replication and/or packaging of the replication-deficient vector. That element, as provided for in the present invention, derives from the packaging function of adenovirus.

It has been shown that a packaging signal for adenovirus exists in the left end of the conventional adenovirus map (Tibbetts, 1977). Later studies showed that a mutant with a deletion in the E1A (194–358 bp) region of the genome grew poorly even in a cell line that complemented the early (E1A) function (Hearing and Shenk, 1983). When a compensating adenoviral DNA (0–353 bp) was recombined into the right end of the mutant, the virus was packaged normally. Further mutational analysis identified a short, repeated, position-dependent element in the left end of the Ad5 genome. One copy of the repeat was found to be sufficient for efficient packaging if present at either end of the genome, but not when moved towards the interior of the Ad5 DNA molecule (Hearing et al., 1987).

By using mutated versions of the packaging signal, it is possible to create helper viruses that are packaged with varying efficiencies. Typically, the mutations are point mutations or deletions. When helper viruses with low efficiency packaging are grown in helper cells, the virus is packaged, albeit at reduced rates compared to wild-type virus, thereby permitting propagation of the helper. When these helper viruses are grown in cells along with virus that contains wild-type packaging signals, however, the wild-type packaging signals are recognized preferentially over the mutated versions. Given a limiting amount of packaging factor, the virus containing the wild-type signals are packaged selectively when compared to the helpers. If the preference is great enough, stocks approaching homogeneity should be achieved.

Retrovirus. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol and env—that code for capsid proteins, polymerase enzyme, and envelope components, respectively. A sequence found upstream from the gag gene, termed Ψ, functions as a signal for packaging of the genome into virions. Two long terminal repeat (LTR) sequences are present at the 5' and 3' ends of the viral genome. These contain strong promoter and enhancer sequences and also are required for integration in the host cell genome (Coffin, 1990).

In order to construct a retroviral vector, a nucleic acid encoding a promoter is inserted into the viral genome in the place of certain viral sequences to produce a virus that is replication-defective. In order to produce virions, a packaging cell line containing the gag, pol and env genes but without the LTR and Ψ components is constructed (Mann et al., 1983). When a recombinant plasmid containing a human cDNA, together with the retroviral LTR and Ψ sequences is introduced into this cell line (by calcium phosphate precipitation for example), the Ψ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is collected, optionally concentrated, and used for gene transfer. Retroviral vectors are able to infect a broad variety of cell types. However, integration and stable expression of many types of retroviruses require the division of host cells (Paskind et al., 1975).

An approach designed to allow specific targeting of retrovirus vectors recently was developed based on the chemical modification of a retrovirus by the chemical addition of galactose residues to the viral envelope. This modification could permit the specific infection of cells such as hepatocytes via asialoglycoprotein receptors, should this be desired.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, the infection of a variety of human cells that bore those surface antigens was demonstrated with an ecotropic virus in vitro (Roux et al., 1989).

Adeno-associated Virus. AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription.

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42–46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

The terminal repeats of the AAV vector can be obtained by restriction endonuclease digestion of AAV or a plasmid such as p201, which contains a modified AAV genome (Samulski et al. 1987), or by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e., stable and site-specific integration. The ordinarily skilled artisan also can determine which minor modifications of the sequence can be tolerated while maintaining the ability of the terminal repeats to direct stable, site-specific integration.

AAV-based vectors have proven to be safe and effective vehicles for gene delivery in vitro, and these vectors are being developed and tested in pre-clinical and clinical stages for a wide range of applications in potential gene therapy, both ex vivo and in vivo (Carter and Flotte, 1996; Chatterjee et al., 1995; Ferrari et al., 1996; Fisher et al., 1996; Flotte et al., 1993; Goodman et al., 1994; Kaplitt et al., 1994; 1996; Kessler et al., 1996; Koeberl et al., 1997; Mizukami et al., 1996; Xiao et al., 1996).

AAV-mediated efficient gene transfer and expression in the lung has led to clinical trials for the treatment of cystic fibrosis (Carter and Flotte, 1996; Flotte et al., 1993). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al., 1996; Flotte et al., 1993; Kaplitt et al., 1994; 1996; Koeberl et al., 1997; McCown et al., 1996; Ping et al., 1996; Xiao et al., 1996).

Other Viral Vectors. Other viral vectors may be employed as expression constructs in the present invention. Vectors derived from viruses such as vaccinia virus (Ridgeway, 1988; Baichwal and Sugden, 1986; Coupar et al., 1988) canary pox virus, and herpes viruses may be employed. These viruses offer several features for use in gene transfer into various mammalian cells.

ii. Non-viral Transfer

DNA constructs of the present invention are generally delivered to a cell, in certain situations, the nucleic acid to be transferred is non-infectious, and can be transferred using non-viral methods.

Several non-viral methods for the transfer of expression constructs into cultured mammalian cells are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979), cell sonication (Fechheimer et al., 1987), gene bombardment using high velocity microprojectiles (Yang et al., 1990), and receptor-mediated transfection (Wu and Wu, 1987; Wu and Wu, 1988).

Once the construct has been delivered into the cell the nucleic acid encoding the therapeutic gene may be positioned and expressed at different sites. In certain embodiments, the nucleic acid encoding the therapeutic gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In a particular embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). The addition of DNA to cationic liposomes causes a topological transition from liposomes to optically birefringent liquid-crystalline condensed globules (Radler et al., 1997). These DNA-lipid complexes are potential non-viral vectors for use in gene therapy.

Liposome-mediated nucleic acid delivery and expression of foreign DNA in vitro has been very successful. Using the β-lactamase gene, Wong et al. (1980) demonstrated the feasibility of liposome-mediated delivery and expression of foreign DNA in cultured chick embryo, HeLa, and hepatoma cells. Nicolau et al. (1987) accomplished successful liposome-mediated gene transfer in rats after intravenous injection. Also included are various commercial approaches involving "lipofection" technology.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear nonhistone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

There are numerous U.S. Patent references describing pharmaceutical delivery employing liposomes. For example, U.S. Pat. No. 5,762,904, incorporated herein by reference, describes the use of polymerized liposomes, methods of preparing the polymerized liposomes and incorporating biologically active substances within the polymerized liposomes, and methods of administering polymerized liposomes containing a biologically active substance to be delivered to a patient are discussed. Additional polymerized vesicles are further described in U.S. Pat. No. 4,587,055 specifically incorporated herein by reference. Viral liposome particles are described in detail in U.S. Pat. No. 4,201,767, specifically incorporated herein by reference.

U.S. Pat. No. 5,759,566 is incorporated herein by reference and describes liposomic dispersions containing proteinaceous substances, that allow the systemic, local or topical administration of drugs by transmucosal route are described. This type of administration is specifically contemplated for use herein. In another embodiments, liposome-nucleic acid complexes for delivery via aerosol with the subsequent in viva expression of a protein encoded by the delivered gene are also contemplated. Such aerosolization provides a convenient method for treating pulmonary disorders, as well as for delivering substances systemically via the lung and are described in greater detail in U.S. Pat. No. 5,756,353, specifically incorporated herein by reference. The Patents discussed above are presented merely by way of examples of the use of liposomes for delivery of nucleic acids, proteins or other therapeutic composition. There are numerous other U.S. Patents that describe the use of liposomes for a therapeutic delivery, as such the use of liposomal delivery of the nucleic acid and or protein compositions of the present invention are well within the skill of the art.

Other vector delivery systems which can be employed to deliver a nucleic acid encoding a therapeutic gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferring (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a cell type such as prostate, epithelial or tumor endothelial cells, by any number of receptor-ligand systems with or without liposomes. For example, the human prostate-specific antigen (Watt et al., 1986) may be used as the receptor for mediated delivery of a nucleic acid in prostate tissue.

In another embodiment of the invention, the expression construct may simply consist of naked recombinant DNA or plasmids. Transfer of the construct may be performed by any of the methods mentioned above which physically or chemically permeabilize the cell membrane. This is applicable particularly for transfer in vitro, however, it may be applied for in vivo use as well. Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding a CAM may also be transferred in a similar manner in vivo and express CAM.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

G. Pharmaceuticals And Methods Of Treating Cancer

In a particular aspect, the present invention provides methods for the treatment of various malignancies. Treatment methods will involve treating an individual with an effective amount of an anti-angiogenic factor protein. The anti-angiogenic factor may be provided as isolated and substantially purified protein in pharmaceutically acceptable formulations using formulation methods known to those of ordinary skill in the art. These formulations can be administered by standard routes. In general, the combinations may be administered by the topical, transdermal, intraperitoneal, oral, rectal or parenteral (e.g., intravenous, subcutaneous or intramuscular) administration. In addition, the anti-angiogenic factor may be incorporated into biodegradable polymers allowing for sustained release of the compound, the polymers being implanted in the vicinity of where drug delivery is desired, for example, at the site of a tumor or implanted so that the anti-angiogenic factor is slowly released systemically.

In an alternative embodiment, the anti-angiogenic factor may be provided as a protein composition for example in an aqueous solution or as a liposomal complex. The discussion of liposomes as delivery vehicles presented above for nucleic acid constructs is equally applicable to delivery of protein or other drug compositions. Further, the anti-angiogenic factor protein may be provided as described above in a viral expression construct containing a gene that encodes said anti-angiogenic factor. An effective amount is described, generally, as that amount sufficient to detectably and repeatedly to ameliorate, reduce, minimize or limit the extent of a disease or its symptoms. More rigorous definitions may apply, including elimination, eradication or cure of disease.

To kill cells, inhibit cell growth, inhibit metastasis, decrease tumor size and otherwise reverse or reduce the malignant phenotype of tumor endothelial cells, using the methods and compositions of the present invention, one would generally contact a "target" cell with the therapeutic expression construct. This may be combined with compositions comprising other agents effective in the treatment of cancer. These compositions would be provided in a combined amount effective to kill or inhibit proliferation of the cell. This process may involve contacting the cells with the expression construct and the agent(s) or factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent.

Alternatively, the gene therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12–24 h of each other and, more preferably, within about 6–12 h of each other, with a delay time of only about 12 h being most preferred. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Administration of the therapeutic expression constructs of the present invention to a patient will follow general protocols for the administration of chemotherapeutics, taking into account the toxicity, if any, of the vector. It is expected that the treatment cycles would be repeated as necessary. It also is contemplated that various standard therapies, as well as surgical intervention, may be applied in combination with the described gene therapy.

Where clinical application of a gene therapy is contemplated, it will be necessary to prepare the complex as a pharmaceutical composition appropriate for the intended application. Generally this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

Aqueous compositions of the present invention comprise an effective amount of the compound, dissolved or dispersed in a pharmaceutically acceptable carrier or aqueous medium. Such compositions can also be referred to as inocula. The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

The compositions of the present invention may include classic pharmaceutical preparations. Dispersions also can be prepared in glycerol, liquid polyethylene glycols, and mixtures thereof and in oils. Under ordinary conditions of storage and use, these preparations contain a preservative to prevent the growth of microorganisms.

Depending on the particular cancer to be, administration of therapeutic compositions according to the present invention will be via any common route so long as the target tissue is available via that route. This includes oral, nasal, buccal, rectal, vaginal or topical. Topical administration would be particularly advantageous for treatment of skin cancers. Alternatively, administration will be by orthotopic, intradermal, subcutaneous, intramuscular, intraperitoneal or intravenous injection. Such compositions would normally be administered as pharmaceutically acceptable compositions that include physiologically acceptable carriers, buffers or other excipients.

In certain embodiments, ex vivo therapies also are contemplated. Ex vivo therapies involve the removal, from a patient, of target cells. The cells are treated outside the patient's body and then returned. One example of ex vivo therapy would involve a variation of autologous bone marrow transplant. Many times, ABMT fails because some cancer cells are present in the withdrawn bone marrow, and return of the bone marrow to the treated patient results in repopulation of the patient with cancer cells. In one embodiment, however, the withdrawn bone marrow cells could be treated while outside the patient with an viral particle that targets and kills the cancer cell. Once the bone marrow cells are "purged," they can be reintroduced into the patient.

The treatments may include various "unit doses." Unit dose is defined as containing a predetermined-quantity of the therapeutic composition calculated to produce the desired responses in association with its administration, i.e., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time. Unit dose of the present invention may conveniently may be described in terms of plaque forming units (pfu) of the viral construct. Unit doses range from $10^3$, $10^4$, $10^5$, $10^6$, $10^7$, $10^8$, $10^9$, $10^{10}$, $10^{11}$, $10^{12}$, $10^{13}$ pfu and higher.

Preferably, patients will have adequate bone marrow function (defined as a peripheral absolute granulocyte count of >2,000/mm$^3$ and a platelet count of 100,000/ mm$^3$), adequate liver function (bilirubin <1.5 mg/dl) and adequate renal function (creatinine <1.5 mg/dl).

i) Cancer Therapy

One of the preferred embodiments of the present invention involves the use of viral vectors to deliver therapeutic genes to cancer cells. Target cancer cells include cancers of the lung, brain, prostate, kidney, liver, ovary, breast, skin, stomach, esophagus, head and neck, testicles, colon, cervix, lymphatic system and blood. Of particular interest are non-small cell lung carcinomas including squamous cell carcinomas, adenocarcinomas and large cell undifferentiated carcinomas.

According to the present invention, one may treat the cancer by directly injection a tumor with a viral vector. Alternatively, the tumor may be infused or perfused with a vector using any suitable delivery vehicle. Local or regional administration, with respect to the tumor, also is contemplated. Finally, systemic administration may be performed. Continuous administration also may be applied where appropriate, for example, where a tumor is excised and the tumor bed is treated to eliminate residual, microscopic disease. Delivery via syringe or catherization is preferred. Such continuous perfusion may take place for a period from about 15 minutes to about 30 minutes, to about 1–2 hours, to about 2–6 hours, to about 6–12 hours, to about 12–24 hours, to about 1–2 days, to about 1–2 wk or longer following the initiation of treatment. Generally, the dose of the therapeutic composition via continuous perfusion will be equivalent to that given by a single or multiple injections, adjusted over a period of time during which the perfusion occurs.

For tumors of >4 cm, the volume to be administered will be about 4–10 ml (preferably 10 ml), while for tumors of <4 cm, a volume of about 1–3 ml will be used (preferably 3 ml). Multiple injections of the anti-angiogenic factor based therapy may be delivered as single dose comprise about 0.1 to about 0.5 ml volumes. The viral particles may advantageously be contacted by administering multiple injections to the tumor, spaced at approximately 1 cm intervals.

In certain embodiments, the tumor being treated may not, at least initially, be resectable. Treatments with therapeutic viral constructs may increase the resectability of the tumor due to shrinkage at the margins or by elimination of certain particularly invasive portions. Following treatments, resection may be possible. Additional viral treatments subsequent to resection will serve to eliminate microscopic residual disease at the tumor site.

A typical course of treatment, for a primary tumor or a post-excision tumor bed, will involve multiple doses of anti-angiogenic factor therapy followed by radiation therapy. Typical primary tumor treatment involves a 6 dose application over a two-week period. The two-week regimen may be repeated one, two, three, four, five, six or more times. During a course of treatment, the need to complete the planned dosings may be re-evaluated.

The radiation therapy used herein includes the use of γ-rays, X-rays, and/or the directed delivery of radioisotopes to tumor endothelial cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate or any analog or derivative variant thereof.

Various combinations may be employed, gene therapy is "A" and the radio- or chemotherapeutic agent is "B":

| A/B/A | B/A/B | B/B/A | A/A/B | A/B/B | B/A/A | A/B/B/B | B/A/B/B |
|-------|-------|-------|-------|-------|-------|---------|---------|
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

H. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Methods

Cell culture. Lewis lung carcinoma cells (LLC-LM), a gift from Dr. Judah Folkman, were maintained in DMEM (Gibco, Grand Island, N.Y.) with 10% heat-inactivated fetal bovine serum (Intergen, Purchase, N.Y.) and penicillin/streptomycin (Gibco, Grand Island, N.Y.)). Human malignant glioma (D54) cell, a gift from Dr. Darell D. Bigher (Duke University Medical Center, Durham, N.C.), were cultured in 50% DMEM, 50% F-12 medium (Gibco, Grand Island, N.Y.), 7% fetal bovine serum and penicillin/streptomycin. SQ-20B squamous cell carcinoma cells, derived from a patient with recurrent squamous cell carcinoma of the larynx were maintained in DMEM: F-12 (3:1), 20% fetal bovine serum, 0.4 μg/ml hydrocortisone (Sigma Chemical Co., St. Louis, Mo.) and penicillin/streptomycin. The SQ-20B cell line forms undifferentiated squamous cell cancer xenografts in nude mice and is relatively radioresistant ($D_0$=239 cGy), when compared with other tumor cell lines. PC3 prostate adenocarcinoma tumor endothelial cells (American Type Culture Collection, Rockville, Md.), were maintained in RPMI-1640 medium (Grand Island Biological Co., Grand Island, N.Y.) containing 10% fetal bovine serum and penicillin/streptomycin. Human aortic endothelial cells (HAEC) and human umbilical vein endothelial cells (HUVEC) were maintained in EGM-2 medium (Clonetics Corporation, San Diego, Calif.).

Angiostatin mouse studies. LLC cells were injected subcutaneously (s.c.) into the right hind limb ($5 \times 10^5$ cells in 100 μl PBS) of C57B1/6 female mice, (Frederick Cancer Research Institute, Frederick. Md.). D54 ($1 \times 10^6$), SQ-20B ($5 \times 10^6$) and PC3 cells ($2 \times 10^7$) were injected into female nude mice. Tumors grew for 17–28 days. Tumor volume was determined by direct measurement with calipers and calculated by the formula ($a \times b \times c/2$). Mice treated with human angiostatin 16 were injected i.p. twice daily (except SQ-20B) at a total dose of 25 mg/kg/day. Mice bearing SQ-20B xenografts received a single injection of human angiostatin (25 mg/kg) 2 h prior to x-irradiation. The inventors found no difference in the response to human angiostatin if it was given in one or two injections daily. One group of mice bearing LLC tumors was injected i.p. twice daily with a dose of 50 mg/kg/day. Mice treated with murine angiostatin received a single injection of either 2.5 mg/kg/day (SQ-20B xenografts) or 25 mg/kg/day (LLC tumors). The care and treatment of experimental animals was in accordance with institutional guidelines. Data are reported as percent of original (day 0) tumor volume and graphed as fractional tumor volume ±S.E.M.

Angiostatin production. Affinity-purified human angiostatin was generated as a cell-free preparation as described (Gately et al., 1997). Testing for the presence of endotoxin was negative for all preparations using the QCL-1000 limulus amebocyte lysate assay (BioWhittaker, Inc., Walkersville, Mich.)).

Murine angiostatin was cloned and expressed using a yeast expression system. Briefly, a cDNA encoding mouse plasminogen, obtained from ATCC, was amplified using Vent DNA polymerase. The primers employed were designed with the appropriate restriction sites to permit cloning directly into the yeast shuttle plasmid pPICZαA, containing Eco R1 and NotI restriction sites. This vector permitted secretion of the recombinant protein into the culture medium. Positive clones were grown in 25 ml BMGY medium containing 100 μg/ml Zeocin at 30° C. for 18–24 h. The overnight grown culture ($A_{600}$, 2–6) was used to inoculate 2 liter flasks containing 500 ml of buffered glycerol medium. Cells were grown for 2 days at 30° C. ($A_{600}$, 16–20), then centrifuged at 500 rpm for 10 min, and resuspended in 300–400 ml of buffered methanol induction medium. The cell-free supernatant was harvested on days 2, 3 and 4 and concentrated using ammonium precipitation (70%), dissolved in 50 mM phosphate buffer pH 7.4 and dialyzed at 4° C. Protein purification was performed using a lysine-Sepharose 4B column (Pharmacia) equilibrated with 50 mM phosphate buffer, pH 7.4. Recombinant angiostatin was eluted with 0.2 M c-amino-N-caproic acid, pH 7.4. Fractions with maximum absorbency were pooled and dialyzed for 25 h against PBS, pH 7.4 at 4° C. with 3 changes at 6–8 h intervals. The dialyzed sample was further concentrated by ultra-filtration using an Amicon contentrator YM 10). Protein concentration was determined using the micro BCA assay (Bio-Rad).

Immunohistochemistry in the angiostatin study. At day 24, mice were euthanized, tumors excised, and fixed in 10% neutral buffered formalin. After embedding in paraffin, 5 μm sections were cut and tissue sections mounted. Briefly, sections were dried, deparaffinized and rehydrated. After quenching endogenous peroxidase activity and blocking with BSA, slides were incubated at 4° C. overnight with a 1:50 dilution rat anti-mouse CD31 monoclonal antibody (Pharmingen, San Diego, Calif.), followed by incubation for one h with biotinylated rabbit anti-rat immunoglobulin (Vector Laboratories Inc., Burlingame, Calif.). Localization of blood vessels was visualized using the Vectastain elite ABC kit, Vector PK-6100 (Vector Laboratories. Inc., Burlingame, Calif.). Slides were dipped in 0.125% osmium tetroxide (Sigma Chemical Co., St. Louis, Mo.) to enhance positivity and counterstained with 1% methyl green (Trevigen, Inc., Gaithersburg, Md.). Ten high power fields (400×) were examined for each tumor section using a Nikon Microphot-FX microscope equipped with a Sony digital camera. Vessels were counted using Macintosh Image Pro-Plus imaging software.

Clonogenic assay. Endothelial cells (HAEC and HUVEC) were grown in EGM-2 medium (Clonetics). Tumor endothelial cell lines (LLC, D54, SQ-20B and PC3) were grown as described. To account for radiation killing, increasing numbers of cells ($10^2$ to $5 \times 10^4$) were plated in 100-mm tissue culture dishes. Eighteen h after plating, angiostatin was added at concentrations of 10 and 100 ng/ml. Four h later, cells were irradiated with doses of 0–900 cGy using a GE Maxitron x-ray generator operating at 250 kV, 26 mA with a 0.5 mm copper filter at a dose rate of 118 cGy/min. Cultures were returned to the incubator for 14–17 days at which time they were stained with crystal violet, colonies counted, and surviving fraction determined. Colonies greater than 50 cells were scored as positive.

Cloning, expression and purification of murine endostatin in *Escherichia coli* and from *Pichia pastoris*. Briefly the sequence encoding the carboxyl terminal portion of the mouse collagen XVIII was PCR™ amplified from the endostatin pBAPak 8 vector (courtesy of B. Olsen) as a template. The amplified DNA fragment (355 bp) was digested with NdeI and XhoI and ligated into the pET17b his expression vector. The expression of recombinant protein in the pET system was carried out according to the manufacturer's specifications.

Mouse endostatin purification. Recombinant endostatin was purified using a Ni-NTA column in the presence of 8 M urea as described in the QIA expressionist manual. Briefly, the bacterial pellet was solubilized in equilibration buffer containing 8 M urea, 10 mM Tris and 100 mM sodium phosphate buffer pH 8.0 for one h at room temperature. The suspension was sonicated 3–4 times, centrifuged at 10,000× g, and the soluble fraction loaded onto a Ni-NTA column. Bound proteins were eluted by sequentially lowering pH of the buffer form pH 8.0 to 6.3, 4.2 and 3.0. Fractions analyzed by SDS-PAGE containing purified endostatin protein were pooled and permitted to slowly refold. During dialysis against PBS, pH 7.4, at 4° C., the protein precipitated out of solution. Endostatin was further concentrated and stored in small aliquots at −70° C. Protein concentration was determined using the BCA assay (Pierce). This suspension was utilized for the in vivo studies.

Soluble endostatin was purified from *Pichia pastoris*. Briefly, the amplified endostatin fragment containing EcoRI and NotI restriction sites was subcloned into a predigested yeast expression vector. The plasmid was linearized with SacI and used for homologous recombination. Recombinants were selected by plating on YPD plates containing 100 μg/ml of Zeocin and clones which grew were then tested for expression. Protein purification of endostatin was carried out using a heparin-agarose column as described by O'Reilly et al. (1997).

Analysis of apoptosis of Annexin-V and Propidium Iodide stained cells. HUVEC were placed in 35 mm tissue culture dishes and grown to 50% confluence. The cells were divided into four treatment groups: 1) control; 2) 900 cGy; 3) 100 ng/ml endostatin; 4) 100 ng/ml endostatin+900 cGy. Endostatin was added to the cultures four h prior to irradiation. Dishes were analyzed at 0, 4, and 24 h. At these times the dishes were rinsed in PBS ad 20 µl Annexin-V/propidium iodide labeling solution was added per dish and a coverslip placed on the dish. The dishes were incubated for 10 min as per the manufacturer's recommendation (Boehringer Mannheim) and then analyzed by fluorescent microscopy using a Zeiss Photomicroscope equipped with a Hamamatsu digital camera connected to a Macintosh computer running QED Image software. Random fields were photographed and 100 nuclei counted for each experimental condition.

Endostatin mouse studies. Xenografts were grown in the hindlimbs of 6–8 wk old athymic female nude mice (Frederick Cancer Research Institute, Frederick, Md.) by subcutaneous inoculation of $5 \times 10^6$ cells suspended in 100 ml phosphate buffered saline (PBS). Tumors were permitted to grow for 11–15 days to a mean volume of $470.3 \pm 28.1$ mm$^3$ (n−51). At day 0, initial tumor volume was determined by direct measurement using calipers as previously described (Hallahan et al., 1995). Subsequently tumor volume was determined twice weekly. Based on the day 0 tumor volume, mice were randomly assigned to treatment groups such that the mean volume of each treatment group was approximately equal. Mice treated with murine recombinant endostatin were injected intraperitoneally with a dose of 2.5 mg/kg three h prior to x-irradiation (5 Gy/day, 4 days/wk to a total dose of 50 Gy). The care and treatment of experimental animals was in accordance with institutional guidelines. Data are reported as percent of original (day 0) tumor volume and graphed as fractional tumor volume ±S.E.M.

Immunohistochemistry in the endostatin study. At day 35, mice were euthanized, tumors excised and fixed in 10% neutral buffered formalin. After embedding in paraffin, 5 µm sections were cut, tissue sections mounted and anti CD31 immunohistochemistry performed. A total of five high power fields (400×) per section were examined using a Nikon Microphot-FX microscope equipped with a Sony digital camera. Vessel counts were determined using Macintosh Image Pro-Plus imaging software as previously described (Mauceri et al., 1998).

Statistical Analysis. Statistical significance was determined using one-way analysis of variance (ANOVA), the Kruskal-Wallis test, and students/test.

Example 2

Effects of Angiostatin and Ionizing Radiation on Primary Tumor Growth

To assess the effects of human angiostatin on primary tumor growth, the inventors treated mice bearing murine Lewis lung carcinoma tumors (LLC) with 25 mg/kg/day or 30 mg/kg/day. The dose of 25 mg/kg/day produced a 38% decrease in mean tumor volume and 50 mg/kg/day reduced mean tumor volume by 54% as compared with untreated controls (day 9; p=0.026). The inventors selected a dose of 25 mg/kg/day of human angiostatin for subsequent studies to permit optimal evaluation of a potential interaction between angiostatin and IR.

The effects of human angiostatin and ionizing radiation (IR) were examined in LLC tumors and in three human tumor xenograft models (D54, SQ-20B and PC3). These tumor endothelial cell lines, which differ in radiation sensitivities and growth kinetics, are derived from tumors in which local failure results in morbidity and mortality. The tumors volumes at the start of treatment ranged from 386 to 1104 mm$^3$ and represented a tumor burden of 2–5.5% of body weight. The dose of 25 mg/kg/day of human angiostatin produced only modest growth inhibition compared with IR alone. By contrast combined treatment with human angiostatin and IR produced significant growth inhibition (determined at the nadir; (FIG. 1) compared with-either treatment alone (Table 4).

In other studies, mice bearing LLC tumors were treated with recombinant murine angiostatin. By day 5, 25 mg/kg/day of murine angiostatin produced a significant decrease (p=0.007) of 29% in mean tumor volume ($1680 \pm 111$ mm$^3$) when compared with control tumors ($2370 \pm 169$ mm$^3$). In mice bearing SQ-20B xenografts (FIG. 1D) treatment with murine angiostatin (2.5 mg/kg/day) and IR significantly reduced mean tumor volume by 64% (day 21; p<0.001) when compared with angiostatin alone (16% reduction) or IR alone (18% reduction). These studies employing murine angiostatin at a ten fold lower dose confirmed the interactive anti-tumor effects of combined treatment with angiostatin and IR.

TABLE 4

Summary of Fractional Tumor Volume as a Function of Treatment

| Tumor Designation | Control | Radiation | Human Angiostatin | Human Angiostatin + Radiation | |
|---|---|---|---|---|---|
| LLC day 9 (n = 28) | 8.49 ± 0.51 | 3.21 ± 0.73 (40 Gy) | 5.85 ± 0.12 | 0.96 ± 0.20 | p < 0.05 |
| D54 day 21 (n = 20) | 9.25 ± 0.91 | 2.78 ± 0.89 (30 Gy) | 2.94 ± 0.07 | 0.38 ± 0.16 | p < 0.005 |
| SQ-20B day 21 (n = 31) | 2.17 ± 0.50 | 1.05 ± 0.31 (56 Gy) | 2.94 ± 0.07 | 0.38 ± 0.16 | p < 0.001 |
| PC3 day 42 (n = 38) | *2.55 ± 0.05 | 0.75 ± 0.35 (40 Gy) | *1.98 ± 0.55 | 0.09 ± 0.05 | p < 0.001 |

Data are reported as mean tumor volume ± SEM per group
day = the nadir of regression
n = the total number of animals
*Mice were sacrificed at day 21 due to tumor burden.

In LLC tumors, the mean fractional volume of 3.21 mm$^3$ (radiation treatment group) represents a 62.2% volumetric reduction. If this percentage is analyzed with the 31.1% reduction in the angiostatin group, then the expected volumetric reduction in the combined treatment group should be 74%. However, the percent reduction in the combined treatment group is 88.7%, which suggests greater than additive treatment effects. Greater than additive treatment effects are also observed in D54 tumors (expected=90.4%, actual=95.9%), SQ-20B tumors (expected=34.4%, actual=82.5%) and PC3 tumors (expected=77.2%, actual=96.5%).

Example 3

Effects of Angiostatin and Radiotherapy on Tumor Neovascularization

To evaluate the effects of treatment on tumor neovascularization, the representative tissue sections from LLC, D54 and SQ-20B tumors were examined using anti-CD31 antibody and standard immunohistochemical techniques. The number of vessels per high power field was reduced following exposure to combined treatment with human angiostatin and IR compared with all other treatments in LLC and D54 tumors. The number of vessels per high power field was also reduced in SQ-20B tumors exposed to combined treatment with angiostatin and IR compared with IR alone (p=0.04). Significant interactive treatment effects were observed in all tumor types [LLC (day 14, p=0.06), D54 (day 24, p=0.01) and SQ-20B (day 28, p=0.003); ANOVA].

Example 4

Cytotoxicity of Combined Angiostatin and Radiotherapy

Figure 2A:
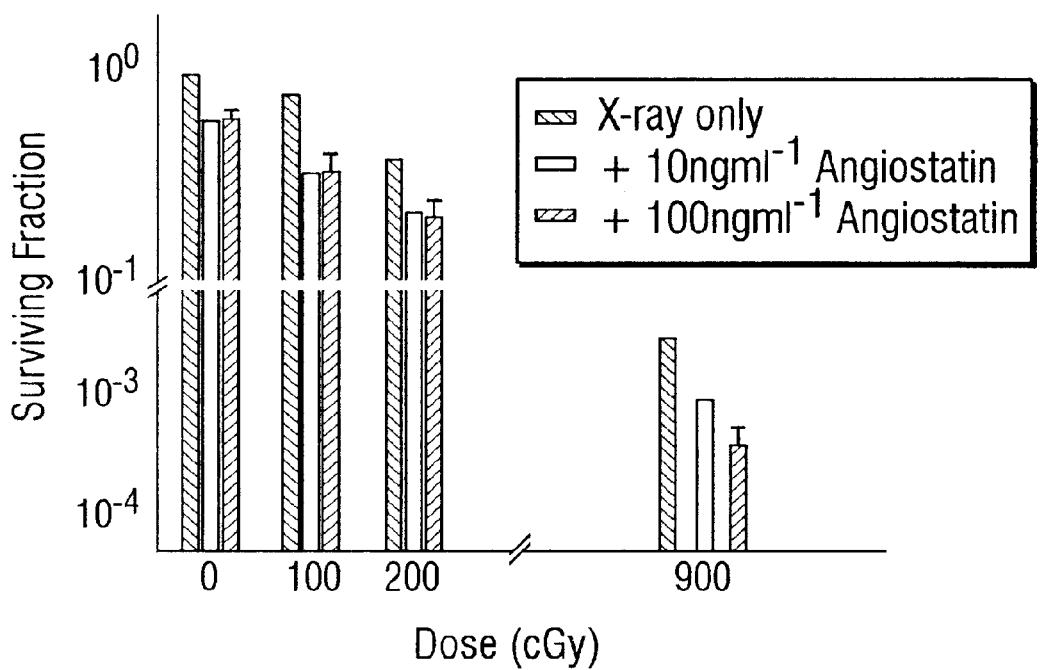
FIG. 2A and FIG. 2B In vitro clonogenic x-ray survival of FIG. 2A) human aortic endothelial cells (HAEC) and FIG. 2B) human umbilical vein endothelial cells (HUVEC) in the presence of human angiostatin. Cells were plated and exposed to angiostatin 4 h prior to a single dose of x-irradiation. Colonies were stained and surviving fraction determined. Data represent the mean of two separate studies ±S.E.M.
Figure 2B:
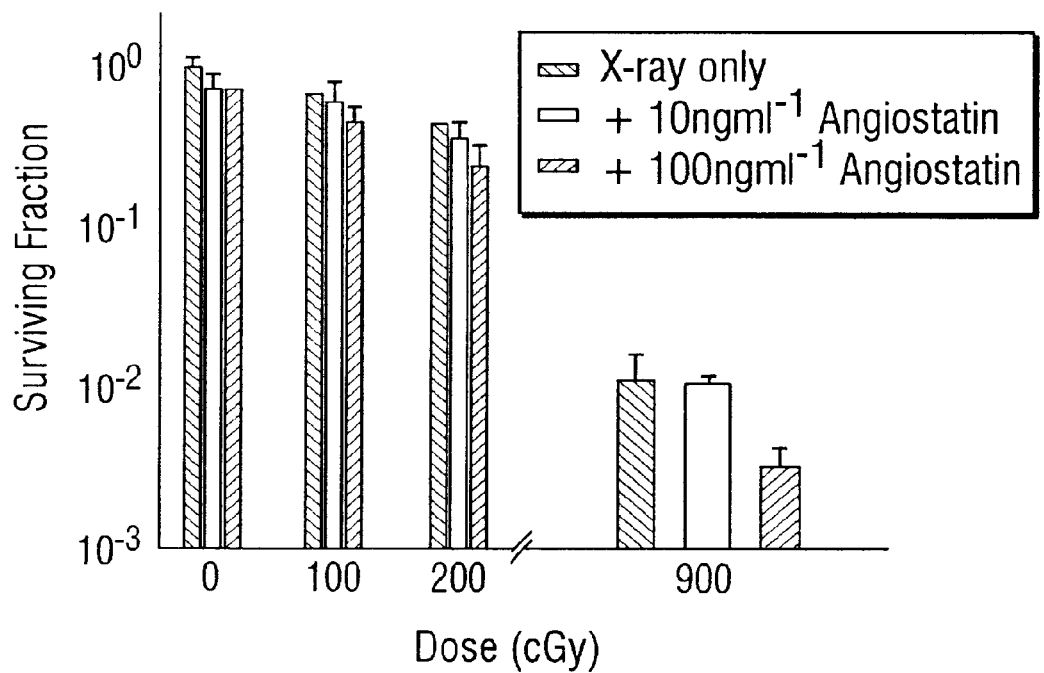
Figure 3A:
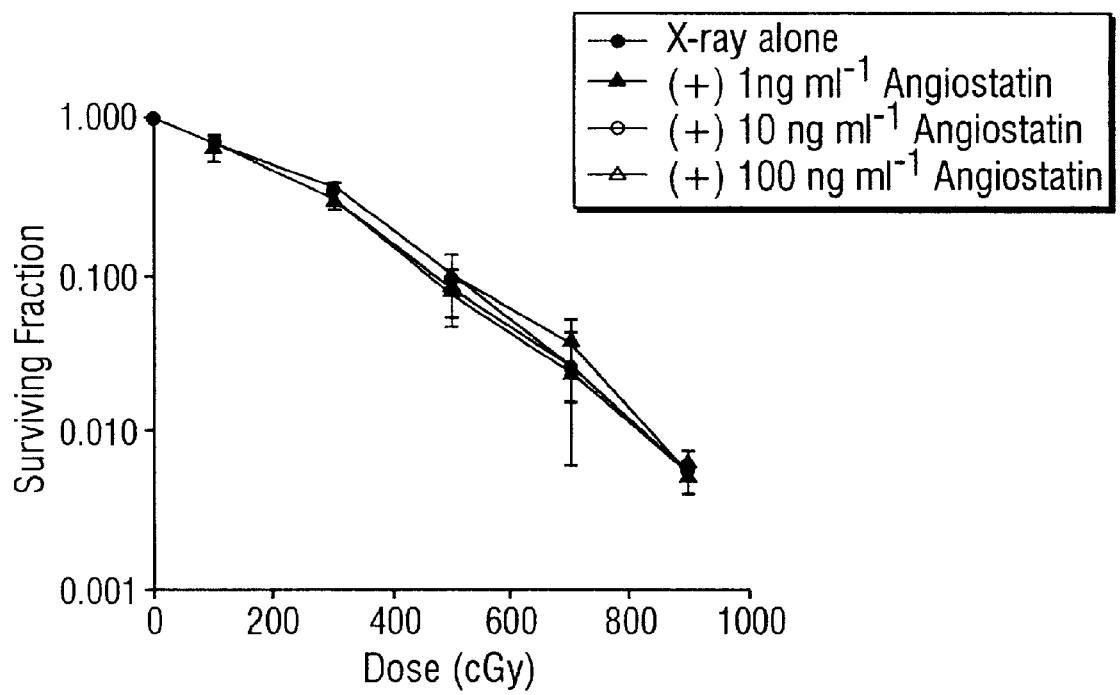
FIG. 3A, FIG. 3B, FIG. 3C and FIG. 3D. In vitro clonogenic x-ray survival of FIG. 3A) Lewis lung carcinoma cell line (LLC), FIG. 3B) human malignant glioma cell line (DS4), FIG. 3C) human squamous cell carcinoma cell line (SQ-20B), and FIG. 3D) human prostate adenocarcinoma cell line (PC3). Cells were plated and exposed to human angiostatin 4 h prior to a single dose of x-irradiation. Colonies were stained and surviving fraction determined as described. Data are represented as the mean ±S.EM.
Figure 3B:
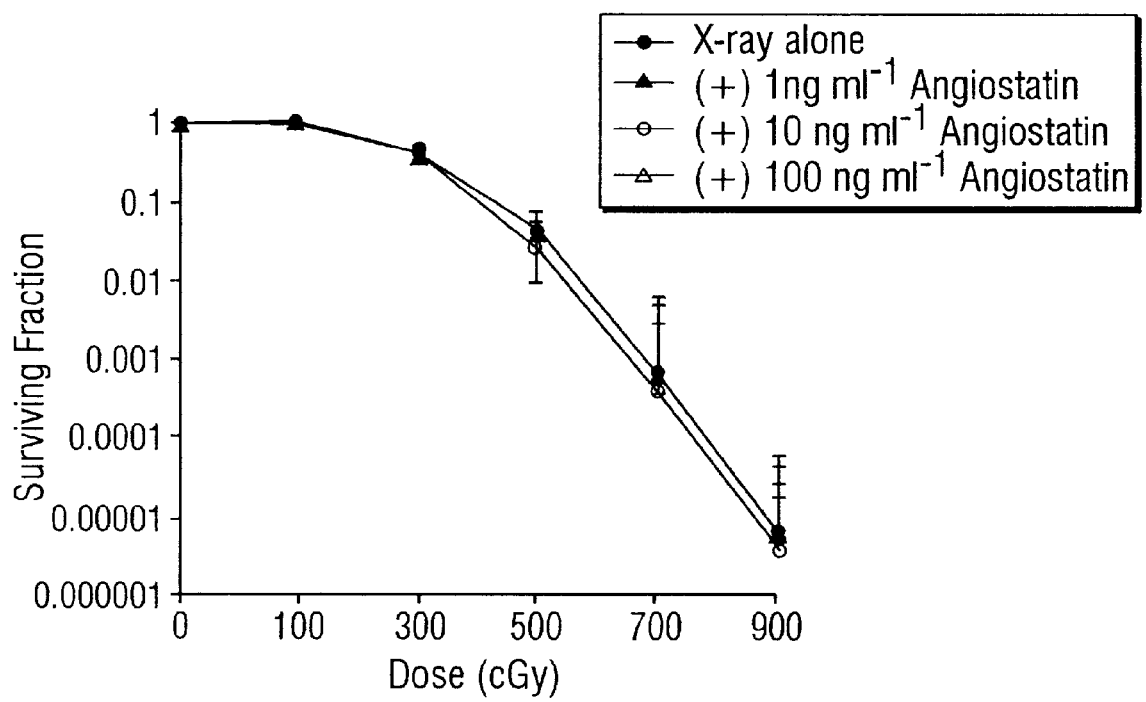
Figure 3C:
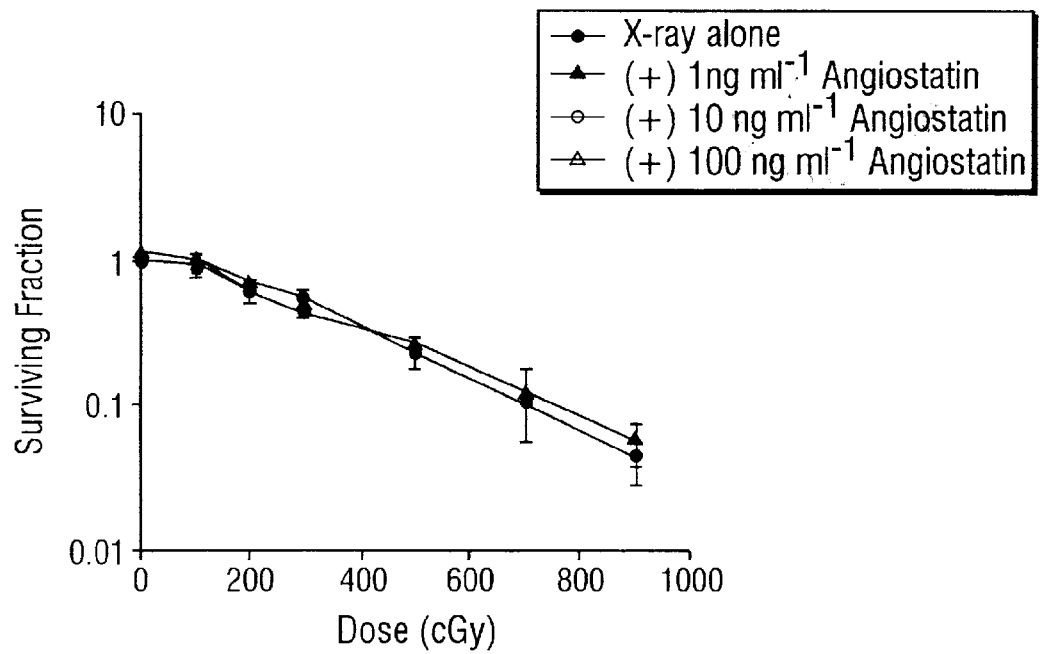
Figure 3D:
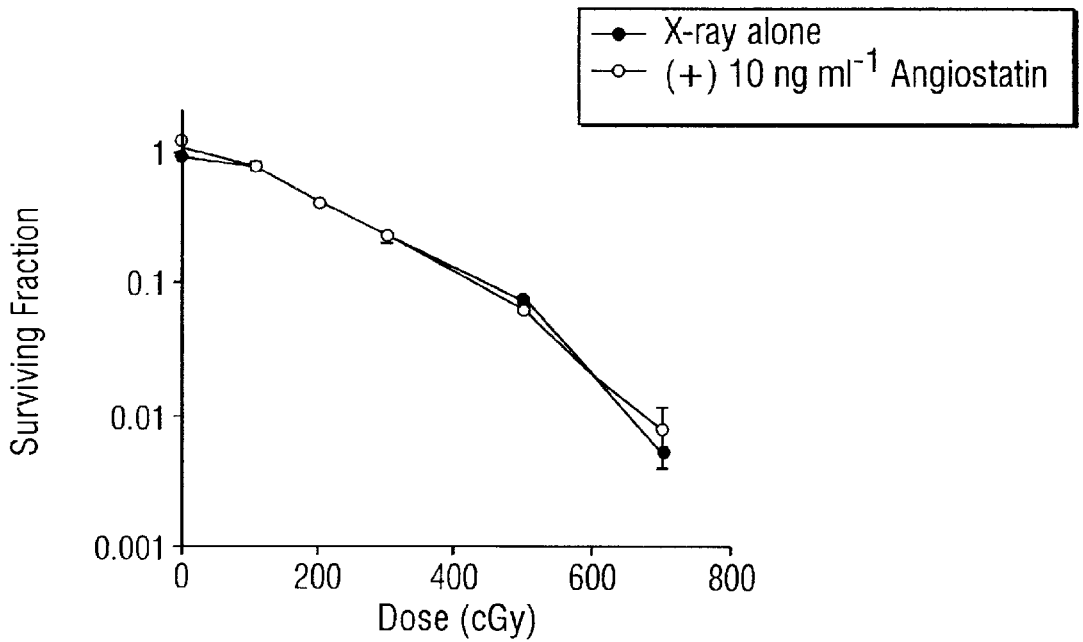

To explore potential cytotoxic effects when angiostatin is combined with IR, clonogenic survival was performed using human aortic endothelial cells (HAEC) and human umbilical cord endothelial cells (HUVEC). Clonogenic assays demonstrated 30 to 40% cell killing for HAEC and HUVEC cells exposed to human angiostatin (10 and 100 ng/ml). There was no difference in the amount of apoptosis as measured by DAPI staining of HUVEC cells at 4, 8, 12, or 24 h of treatment with angiostatin (6.03–9.92%) compared with control HUVEC cells (6.03–10.57%). Interactive cytotoxicity was observed when HAEC and HUVEC were treated with angiostatin and exposed to 100, 200, and 900 cGy (FIG. 2). Similar results were obtained when bovine aortic endothelial cells (BAEC) were treated with human angiostatin and IR. By contrast, no cytotoxicity was observed when tumor endothelial cell lines were treated with human angiostatin, and no interactive killing was observed following exposure to angiostatin and IR (FIG. 3). No increase in apoptosis was observed when HUVEC cultures were treated with angiostatin and IR (maximum of 21.58% at 4 h) compared with IR alone (maximum of 22.54% at 4 h). These findings indicate that the interactive cytotoxic effects of human angiostatin and IR in vitro are selective for endothelial cells and not mediated by apoptosis.

The anti-tumor interaction of angiostatin and IR were observed at concentrations of angiostatin, which produced modest effects on primary tumor growth. The inventors treated with angiostatin for a relatively short period of time (to coincide with radiotherapy) and used lower doses than those employed in previous reports (O'Reilly et al., 1996). The relative lack of treatment effects when angiostatin was used as a single agent may be related to the large tumor volumes employed in studies compared to other studies (Holmgren et al., 1995; Sim et al., 1997). Analysis of histological sections of tumors treated with angiostatin and IR suggests that newly forming vessels are the target of the observed anti-tumor effects. This hypothesis is supported by in vitro studies, which demonstrate interactive killing between angiostatin and IR in endothelial cell lines. Further support for the endothelial cell as a target of the radiation/angiostatin interaction is provided by studies which demonstrate no cytotoxic action or radiosensitizing effects of angiostatin in tumor endothelial cell lines. Angiostatin inhibits endothelial cell proliferation in vitro; however, this is the first report to describe clonogenic killing of endothelial cells by angiostatin and synergistic anti-tumor effects with angiostatin as a radiation modifier. Angiostatin has great promise to enhance the therapeutic ratio in combined modality cancer treatment.

Example 5

The Effects of Endostatin on Angiogenesis

Figure 4A:
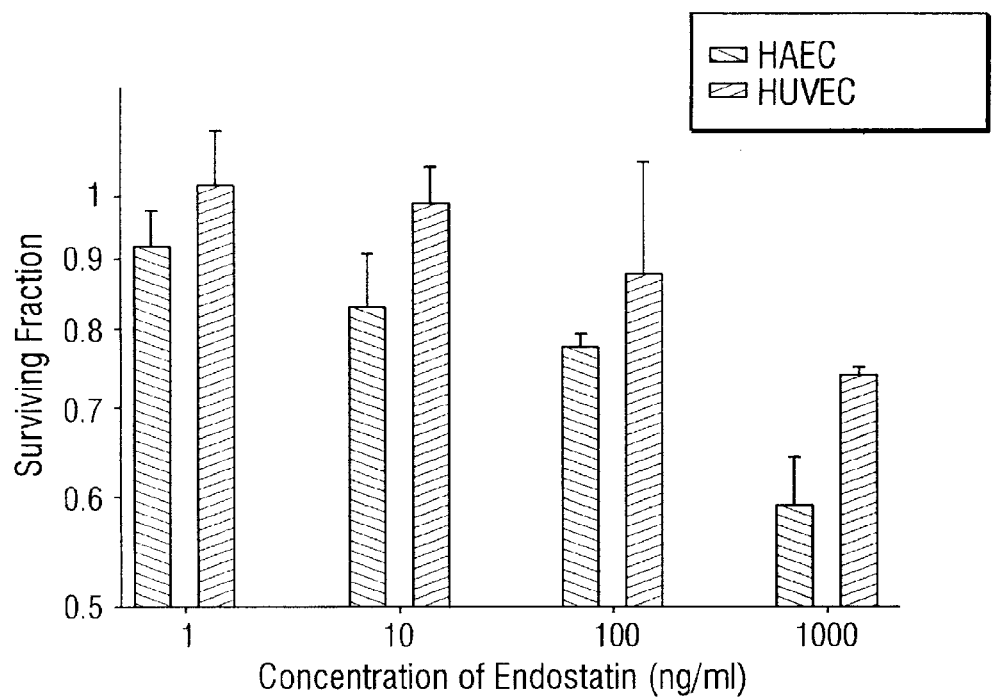
FIG. 4A and FIG. 4B.

To explore potential cytotoxic effects of endostatin in vitro, clonogenic survival analysis was performed using human aortic endothelial cells (HAEC), human umbilical cord endothelial cells (HUVEC) and SQ-20B tumor endothelial cells. Clonogenic assays demonstrated 30 to 40% killing for HAEC and 10–20% killing in HUVEC cells exposed to concentrations of 10 and 100 ng/ml of endostatin (FIG. 4A). To explore the mechanism of endothelial cell killing, HUVEC cells were stained with the combination of Annexin-5 and propidium iodide. Exposure to 100 ng/ml endostatin produced 41.9% apoptosis at 8 h, while 14.8% apoptosis was seen in untreated controls. No cytotoxicity was observed when the epidermoid carcinoma SQ-20B tumor cells were treated with endostatin.

Example 6

Interactions of Endostatin and Ionizing Radiation

Figure 4B:
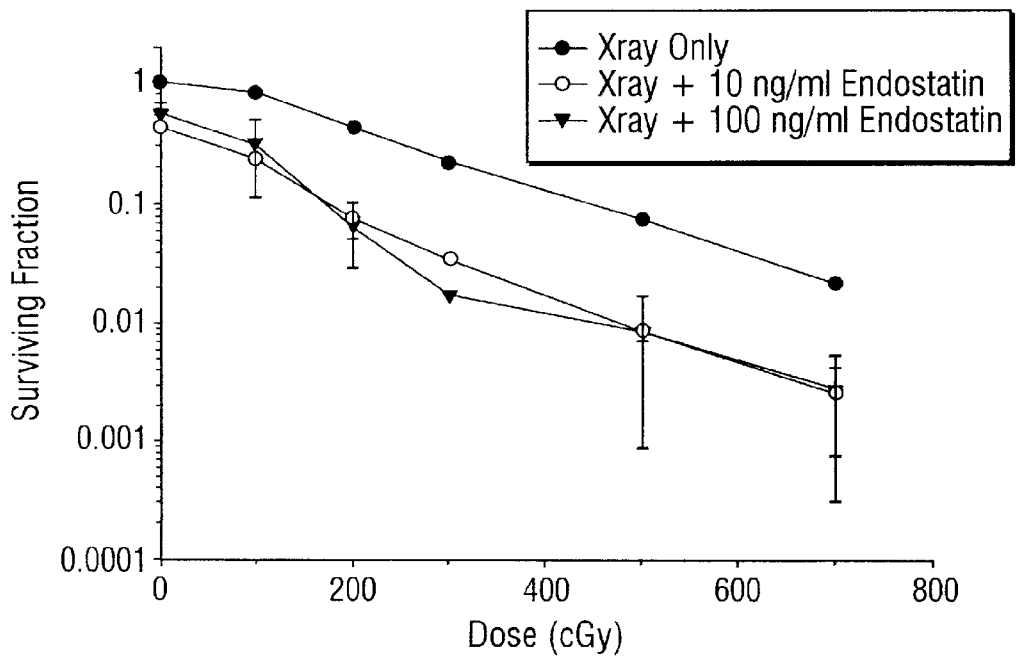

To explore potential interactive cytotoxicity between endostatin and IR, HAEC and HUVEC cultures were treated with endostatin and exposed to 100–700 cGy (FIG. 4B shows the results using HAEC). Both 10 and 100 ng/ml of endostatin produced enhancement of radiation-mediated cytotoxicity of HAEC cells from 100 to 700 cGy. In addition, enhancement of radiation-mediated cell killing by 100 ng/ml endostatin in HUVEC cells occurred at the highest radiation dose (700 cGy). These data demonstrate interactive cytotoxicity between endostatin and IR in both HAEC and HUVEC cell lines. No interactive killing was observed when SQ-20B tumor cells were treated with the combination of endostatin and IR.

Figure 5:
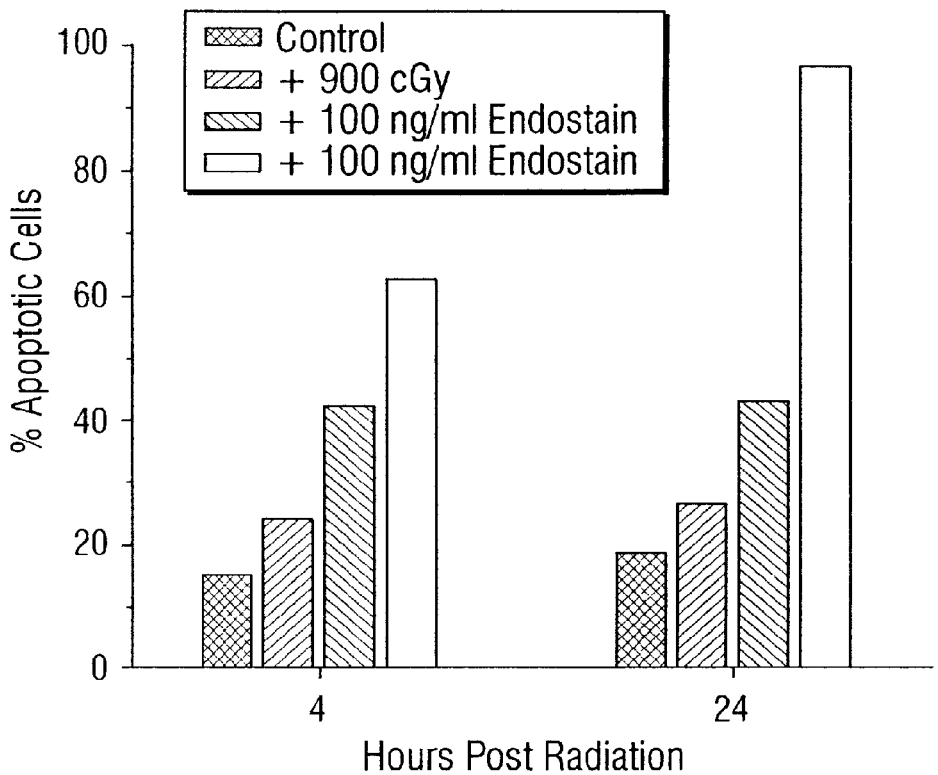
FIG. 5. Endothelial cells were plated in 35 mm tissue culture and were treated using four conditions: 1) control; 2)+900 cGy; 3)+100 ng/ml endostatin; 4)+100 ng/ml endostatin+900 cGy. Four and 24 h after irradiation the unfixed cells were stained with Annexin-V and propidium iodide. Annexin-stained cells indicated early apoptosis while the propidium iodide was used for distinguishing condensed nuclei indicative of late apoptosis.

To evaluate if the cytotoxic interaction between endostatin and IR induced cell killing is mediated by apoptosis. HUVEC cells were treated with 100 ng/ml endostatin, 900 cGy, or the combination. An increase in apoptosis was seen at 4 h in the combined treatment group (62.2%) compared with endostatin alone (41.9%). IR alone (24.1%) or control cells (14.8%). By 24 h, more than 90% of the HUVEC cells treated with endostatin and IR were apoptotic. 18.6% cumulative apoptosis was present in the control group, 42.8% in the endostatin alone group and 50.5% in the radiation alone treatment group (FIG. 5 describes the cumulative at 4 and 24 h). These data suggest that endostatin and IR interact to increase endothelial cell apoptosis to a greater extent than either treatment alone.

Figure 6:
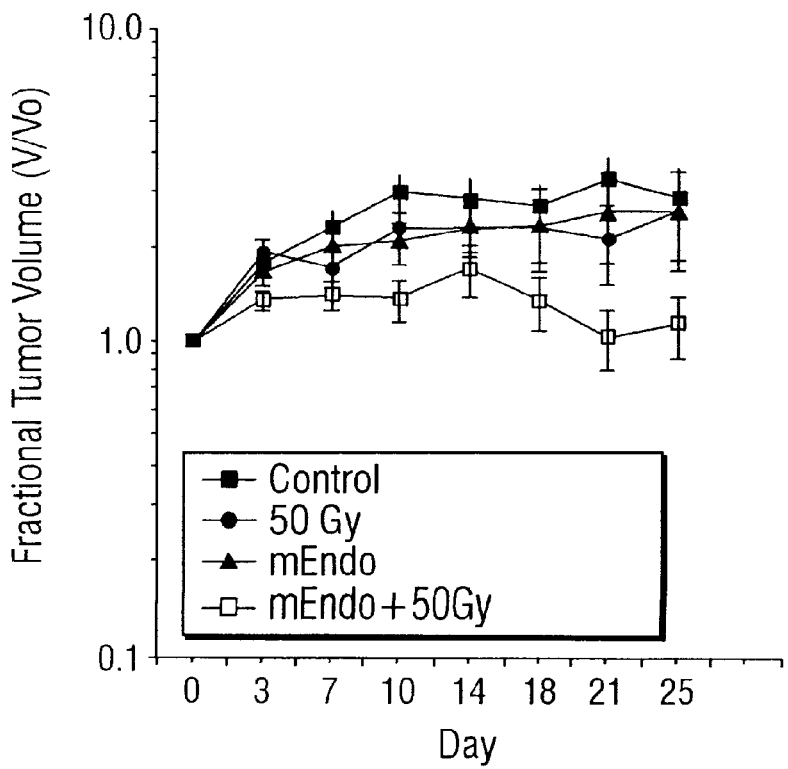
FIG. 6. Tumor growth following combined treatment with endostatin and radiation. Athymic nude mice bearing SQ-20B xenografts (470.3±2 8.1 mm$^3$) were injected intraperitoneally with murine recombinant endostatin (2.4 mg/kg) 3 h prior to x-irradiation (5 Gy/day, 1 days/wk to a total dose of 50 Gy). Data are calculated as the percent of original volume (day 0) tumor volume and graphed as fractional tumor volume ±S.E.M. Volumes of xenografts are shown following treatment with: Control (untreated); radiation alone at 50 Gy; murine endostatin alone (mEndo); murine endostatin and 50 Gy (mEndo 50 Gy).

The inventors employed tumor volume reduction and regression to evaluate potential in vivo interactive cytotoxic effects between endostatin and IR using the SQ-20B xenograft model. Combined treatment with endostatin and IR produced tumor growth inhibition which was most pronounced at the nadir of regression (day 21) when compared with all other treatments (FIG. 6). Compared with untreated control tumors, 50 Gy produced a 36% reduction in mean tumor volume, while treatment with endostatin alone produced a 21% reduction. Following combined treatment with endostatin and 50 Gy mean tumor volume was reduced by 69% when compared with control (p=0.06, ANOVA). Mice in both the control and IR treatment groups were sacrificed at day 25 due to tumor burden. The remaining two treatment groups were followed until day 35, at which time tumor tissue was collected for immunohistochemical analysis. Tumors receiving combined treatment with endostatin and IR (443±95 mm$^3$) were 47% smaller than tumors treated with endostatin alone (832±342 mm$^3$). To evaluate the effects of combined treatment with endostatin and IR on the tumor vasculature, the inventors examined tumor tissue sections using anti-CD31 antibody and standard immunohistochemical techniques. Tumors were excised from six animals in the two surviving treatment groups (endostatin alone and endostatin+IR.) The mean number of vessels per five high power fields was reduced following exposure to combined treatment with endostatin and IR (14±8) compared with endostatin alone (40±11; p=0.09).

The hypothesis that the endothelium is a potential target for the cytotoxic interaction between endostatin and IR is supported by in vitro studies which demonstrate that the IR/endostatin combination sensitizes endothelial cells to killing, by increasing apoptosis. The in vivo studies provide additional support for the hypothesis that the tumor endothelium can become a therapeutic target. Tumor regression observed following combined treatment with endostatin and IR in the present study suggests interactive antitumor effects that are greater than additive. In the present studies, endostatin was administered for only 10 days to coincide with fractioned radiation and the concentrations of endostatin used (2.5 mg/kg/day) were relatively low. In comparison Boehm et al. injected tumor bearing animals with 20 mg/kg/day (Boehm et al., 1997). Taken together, the present data suggest that treatment with anti-angiogenic peptides, such as endostatin, which synergizes with IR, can magnify tumor control by causing endothelial cell killing which deprives the growing tumor of an adequate blood supply. Radiotherapy combined with anti-angiogenic therapy offers considerable potential for the treatment of human cancers.

Example 7

Ad.mIL-12 Increases Anti-tumor Effects of Ionizing Radiation

Figure 7:
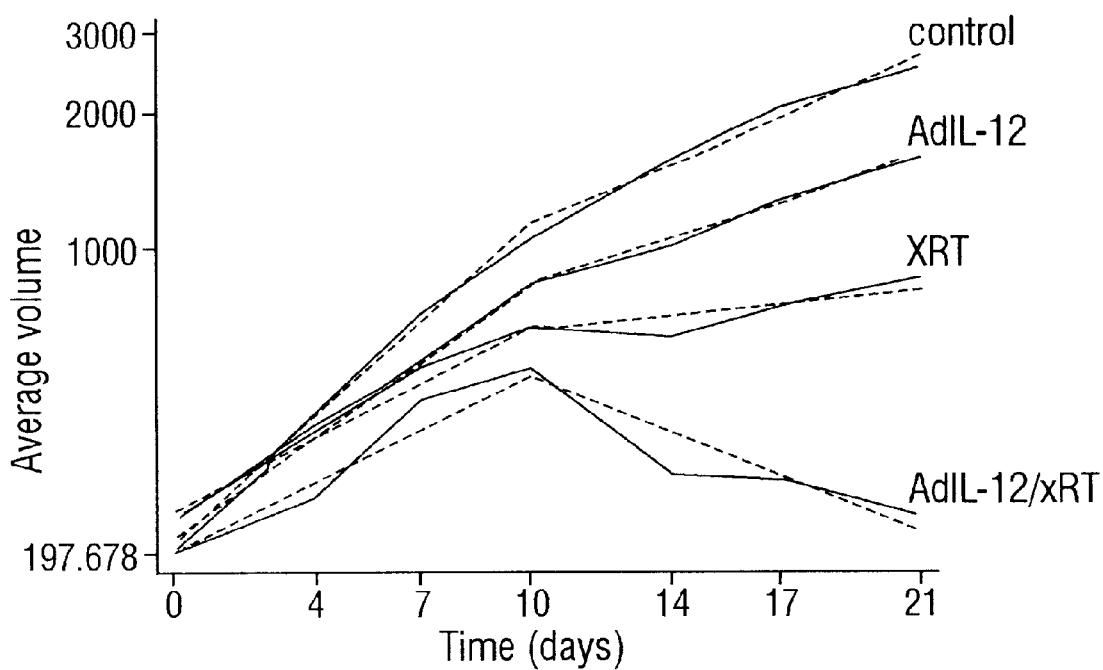
FIG. 7. Mean right-limb volume, with fitted model. Average tumor volume (mm$^3$) is plotted against time (days).

The inventors treated mouse hind limb Ag 104 tumors with intratumoral Ad.mIL-12 and fractionated radiation delivered as 5 Gy/day, 4 days/week for a total of 20 Gy. Mice were sacrificed at 60 days after starting treatment and/or when hind limb tumor volumes measured greater than $2000^{mm3}$. Untreated control tumors grew to a mean volume of 2000 mm by day 21. No spontaneous tumor regressions were observed. Also no evidence of systemic toxicity due to any combination of adenoviral gene therapy and radiation was observed in the three treatment trials. Complete regression rates were defined as the number of tumor volumes equal to zero divided by the number of tumors in each treatment group by day 60. Overall, 26 of 44 (59%) tumors treated with Ad.mIL-12 plus radiation had completely regressed compared to 14 of 53 (26%) tumors treated with radiation alone, 3 of 14 (21%) tumors treated with Ad.null plus radiation, and 11 of 51 (22%) tumors treated with Ad.mIL-12 alone. At 60 days the estimated percentage of regressions increased from 23% in the radiation only group to 61% in the combined treatment group. Radiation increased the probability of complete regression by a factor of 7.5 (3.3–17.3:p<0.001) and Ad.mIL-12 by a factor of 5.3 (2.4–11.7; p<0.001) compared to groups treated with no radiation. A piecewise linear regression was fit to the logarithm of the mean tumor volume for each treatment group (FIG. 7). Before day 10 following intratumoral injection of IL-12 and IR, treatment groups had similar tumor volume growth rates. After day 10, the tumor doubling time for tumors treated with Ad.mIL-12 plus radiation was significantly prolonged compared to all other treatment groups (p<0.001, Table 5). Taken together, these data support a synergistic interaction between IL-12 and irradiation.

TABLE 5

| Treatment Group | Estimated doubling times (in days) | | |
|---|---|---|---|
| | Estimate | 95% CI | |
| Before day 10 | | | |
| Control | 4.1 | (3.6, 4.6) | |
| AdIL2 | 5.1 | (4.6, 5.8) | |
| XRT | 7.3 | (6.5, 8.3) | |
| Ad/XRT | 8 | (6.4, 10.8) | |
| AdIL12/XRT | 7.6 | (6.5, 9.1) | |
| After day 10 | | | |
| Control | 9.1 | (8.1, 10.3) | |
| AdIL12 | 11.4 | (9.3, 14.6) | |
| XRT | 33.5 | (18.9, 145.9) | |
| Ad/XRT | 13.9 | (8.4, 38.8) | |
| AdIL12/XRT | 9.4 | (−15.3, −6.8) | |

Example 8

Ag 104 and Tumor Vascularity

To study the potential anti-angiogenic effect of IL-12, the inventors evaluated with anti-CD31 staining representative Ag 104 tumor sections obtained at day 3, 7 and 21 of treatment. Data demonstrate increased vascularity in an untreated tumor compared to a tumor treated with Ad.mIL-12 with radiation at day 21. Average vessel counts in tumor sections were 7.9, 7.0, 3.7 and 2.3 per high power field for untreated control, radiation, Adm.IL-12 and Adm.IL-12 plus radiation groups respectively. Vessel counts in the untreated control group were significantly higher than in either the Adm.IL-12 group (p<0.001) or the Adm.IL-12 plus radiation group (p<0.001). The average number of vessels was also higher in the radiation only group compared to the Adm.IL-12 plus radiation group (p=0.058).

Example 9

IL-12 and IFN-y in Ag 104 Tumors

The inventors next determined induction of IL-12 and IFNγ in the tumors with ELISAs specific for murine IL-12 and IFN-y. Murine IL-12 and IFN-y were detectable in control and treated Ag 104 tumors. Peak concentrations of IL-12 (50.000 pg/μg protein) were found in tumors treated with Ad.mIL-12 on day 3, that decreased to 10.000 pg/μg protein by day 21. Concentrations of marine IL-12 were lower in tumors treated with radiation, Ad.null plus radiation and Ad.mIL-12 plus radiation compared to tumors treated with Ad.mIL-12 alone. Levels of IL-12 in all treatment groups progressively decreased from day 3 through 21. Tumors treated with Ad.mIL-12 plus radiation exhibited a peak level of IFN-y at day 7 (8000 pg/μg protein) compared to tumors treated with Adm.IL-12 alone (3,000 pg/μg protein). Untreated control tumors had higher levels of IL-12 compared to IFN-y levels.

Example 10

Distant Control of Tumors with Ad.mIL-12 and Radiation

Figure 8:
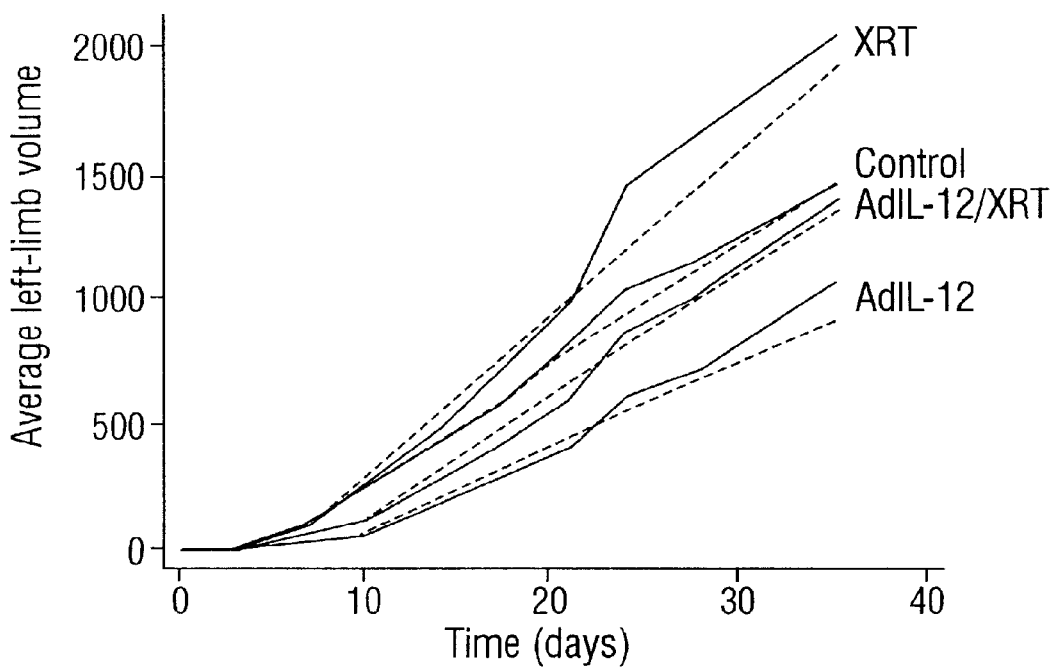
FIG. 8. Average left-limb volume, with fitted model. Average left-limb volume (mm$^3$) is plotted against time (days).
Figure 9A:
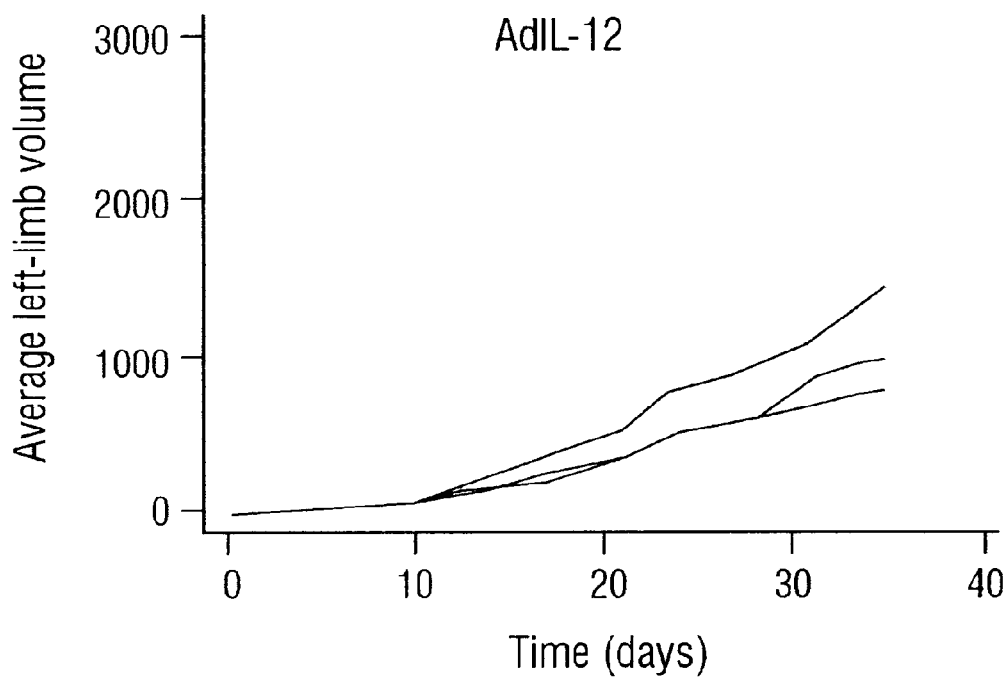
FIG. 9A, FIG. 9B, FIG. 9C and FIG. 9D. Average left-limb volume, by size of right tumor on Day 3. Average left-limb volume (mm$^3$) is plotted against time (days).
Figure 9B:
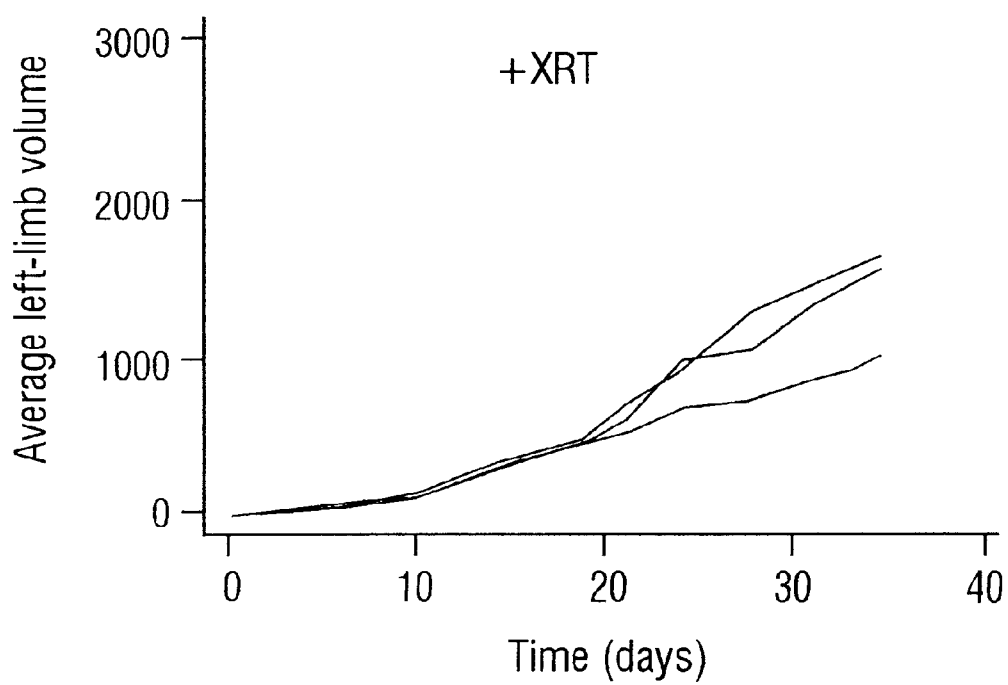
Figure 9C:
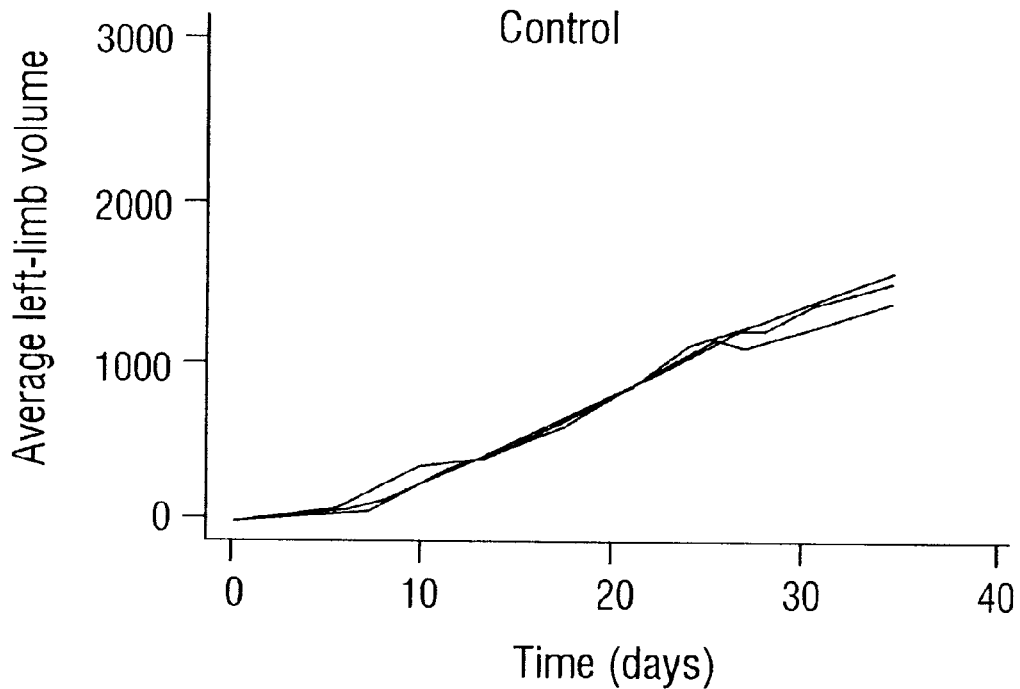
Figure 9D:
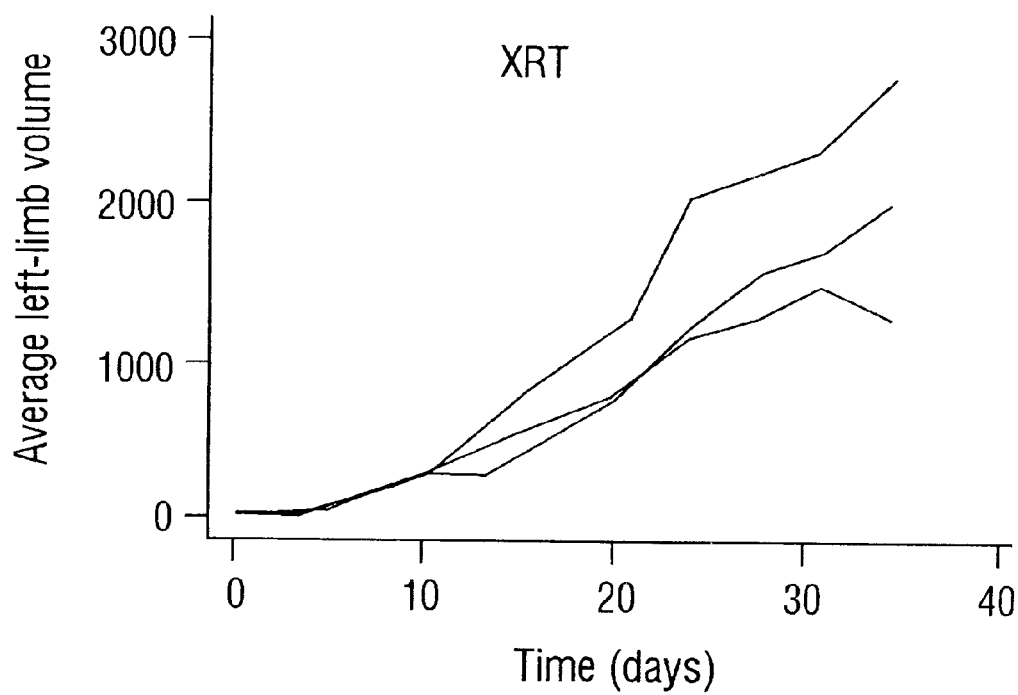

Because IL-12 stimulates immune responses, the inventors studied if injection of Ad.mIL-12 into Ag 104 tumors has a therapeutic effect on untreated tumors at a distant site. The inventors treated right hind limb Ag 104 tumors with radiation alone, Ad.mIL-12 alone, Ad.null plus radiation, and concurrently injected either $1\times10^5$, or $5\times10^6$ Ag 104 cells into the opposite flank. Mice were sacrificed at 35 days after starting treatment and/or when hind limb tumor volumes measured greater than 2000 mm$^3$. All right hind limb tumors which were untreated grew to a mean volume of 2000 mm$^3$, by day 21. By day 21, left hind limbs injected with $1\times10^5$ Ag 104 cells grew tumors to a higher mean volume than left limbs injected with $5\times10^6$ cells. In animals injected with $5\times10^6$ Ag 104 cells, 19/19 (100%) left hind limb tumors were induced by day 35 in the control group, 14/21 (67%) in the group treated with Ad.mIL-12 alone, 19/21 (90%) in the group treated with radiation alone, and 16/21 (76%) in the group treated with Ad.mIL-12 plus radiation. Thus, Ad.mIL-12 was estimated to reduce the odds of tumor induction in the opposite flank on day 35 by 87% (37%–97%; p=0.011), whereas radiation appeared to have no effect (p=0.975). Similar effects were observed in mice injected with $10^5$ cells. A linear regression was fit to the mean tumor volume in mice injected with $5\times10^6$ Ag 104 cells starting on day 10 (FIG. 8). Treatment of tumors in the right flank with Ad.mIL-12 alone significantly decreased the mean left limb tumor volume (p=0.030). Thus, the estimated mean volume of tumor in the non-injected non-irradiated limb at day 35 for the group treated with Ad.mIL-12 plus radiation was smaller (p=0.003) than the radiation alone group. Among animals injected with $5\times10^6$ cells receiving Ad.mIL-12 or Ad.mIL-12 and IR animals with the largest right-limb tumors on day 3 had left-limb tumors that grew at slower rates (FIG. 9).

Radiation and IL-12 did not suppress growth on the contralateral limb as effectively as in animals treated with Ad.mIL-12—12 alone. FIG. 8, FIG. 9A, FIG. 9B, FIG. 9C, and FIG. 9D, demonstrate that when right limb volumes are analyzed as a function of treated group tumors (Ad.mIL-12, Ad.mIL-12 +radiation) larger residual masses in the right limb produced were pronounced suppression in the left limb. No consistent relationship between tumor mass and contralateral suppression was observed in the group treated with radiation alone or the untreated control group. These data taken together with data on higher IL-12 levels in mice that received IL-12 alone and had residual local tumors suggest that the extent of IL-12 production is an increase determent of distant tumor growth.

Example 11

Antitumor Immunity After Ad.mIL-12-12 Induced Tumor Regression

The inventors rechallenged successfully treated, tumor-free mice 30 days after complete primary tumor regression by injection of $5\times10^6$ Ag 104 cells into the opposite flank. Mice were observed for tumor growth for an average of 160 days. None of the 9 (0%) animals treated with Ad.mIL-12 alone and only 4 of 15 (27%) animals treated with Ad.mIL-12 plus radiation responded to the challenge of antitumor growth by day 29. Meanwhile, tumors were induced in 6 of 6 (100%) irradiated tumors, and 3 of 3 (100%) tumors treated with Ad.null plus radiation. These findings support the establishment of long-term specific immunity. To test whether the antitumor effect of Ad.mIL-12 with radiation is a result of a CD8+immune response, the inventors depleted CD8+lymphocytes in 3 mice successfully treated with Ad.mIL-12 plus radiation. Tumors developed in all CD8+ depleted animals 7 days after inoculation of $1\times10$ Ag 104 cells. By contrast, mice injected with control antibody did not develop any tumors.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,359,046
U.S. Pat. No. 5,639,725
U.S. Pat. No. 5,733,876
U.S. Pat. No. 5,801,156
U.S. Pat. No. 5,859,018
U.S. Pat. No. 5,861,484
U.S. Pat. No. 5,874,542
Arap et al., *Cancer Res.*, 55:1351–1354, 1995.
Arcone et al., 1988.
Baichwal and Sugden, In: *Gene Transfer*, Kucherlapati R, ed., New York, Plenum Press, pp. 117–148, 1986.
Bartlett et al., *Proc. Natl. Acad. Sci. USA*, 93:8852–8857, 1996.
Bedzyk et al., *J. Biol. Chem.*, 265:18615, 1990
Benvenisty and Neshif, *Proc. Nat. Acad. Sci. USA*, 83:9551–9555, 1986., 1992.
Boehm, Folkman, Browder, "Antiangiogenic therapy of experimental cancer does not induce acquired drug resistance," *Nature*, 390:404–407, 1997.
Caldas et al., *Nat. Genet.*, 8:27–32, 1994.
Cao et al., *J. Biol. Chem.*, 271:29461–29467, 1996.
Carter and Flotte, *Ann. N. Y. Acad. Sci.*, 770:79–90, 1995.
Chatterjee, et al., *Ann. N.Y. Acad. Sci.*, 770:79–90, 1995.
Chaudhary et al. *Proc. Natl. Acad. Sci.*, 87:9491, 1990
Chen and Okayama, *Mol. Cell Biol.*, 7:2745–2752, 1987.
Cheng et al., *Nature*, 379:554, 1996.
Cheung et al., *J. Biol. Chem.*, 268:6139–6146, 1993.
Coffin, In: *Virology*, ed., New York: Raven Press, pp. 1437–1500, 1990.
Coupar et al., *Gene*, 68:1–10, 1988.
Dani, et al., *J. Biol. Chem.*, 264:10119–10125, 1989.
Denekamp and Hill, "Angiogenic attack as a therapeutic strategy for cancer," *Radiother. Oncol.*, 20:103–112, 1991.
Dubensky et al., *Proc. Nat. Acad. Sci. USA*, 81:7529–7533, 1984.
Fechheimer et al., *Proc. Natl. Acad. Sci. USA*, 84:8463–8467, 1987.
Ferkol et al., *FASEB J.*, 7:1081–1091, 1993.
Ferrari et al., *J. Virol.*, 70:3227–3234, 1996.
Fidler and Balch, *Curr. Probl. Surg.* 24:137–208, 1987.
Fidler and Ellis, *Cell*, 79:185–188, 1994.
Fidler and Poste, *Semin. Oncol.* 12:207–221, 1985.
Fidler, *J. Natl. Cancer Inst.*, 87:1588, 1995.
Fisher et al., *J. Virol.*, 70:520–532, 1996.
Flotte et al., *Proc. Natl. Acad. Sci. USA*, 90:10613–10617, 1993.

Folkman and Shing, "Angiogenesis," *J. Biol. Chem.,* 267:10931–10934, 1992.
Folkman and Shing, *J. Biol. Chem.,* 267:10931–10934, 1992.
Folkman, "Angiogenesis and angiogenesis inhibition: an overview," *Jpn. J. Pharmacol.,* 73:59–71, 1997.
Folkman, "Angiogenesis in cancer, vascular, rheumatoid and other disease," *Nature Medicine,* 1:27–31, 1995.
Folkman, *Cancer Res.* 46, 467–473, 1986.
Folkman, *N Engl J Med.* 285(21): 1182–1186, 1971
Folkman, *N Engl J Med.* 320(18): 1211–1212, 1989
Folkman, *Nature Med.,* 1:27–31, 1995.
Fraley et al., *Proc. Natl. Acad. Sci. USA,* 76:3348–3352, 1979.
Gastl et al., "Angiogenesis as a target for tumor treatment," *Oncology,* 54:177–184, 1997.
Gately et al., *Proc. Natl. Alcad. Sci. USA,* 94:10868–10872, 1997.
Ghosh and Bachhawat, *In: Liver diseases, targeted diagnosis and therapy using specific receptors and ligands,* (Wu G, Wu C ed.), New York: Marcel Dekker, pp. 87–104, 1991.
Goodman et al., *Blood,* 84:1492–1500, 1994.
Gopal, *Mol. Cell Biol.,* 5:1188–1190, 1985.
Gossen and Bujard, *Proc. Natl. Acad. Sci. USA,* 89:5547–5551, 1992.
Gossen et al., *Science,* 268:1766–1769, 1995.
Graham and Van Der Eb, *Virology,* 52:456–467, 1973.
Hallahan et al., "Spatial and temporal control of gene therapy using ionizing radiation," *Nat. Med.,* 1:786–791, 1995.
Hanahan and Folkman, "Patterns and emerging mechanisms of the angiogenic switch during tumorigenesis," *J. Natl. Cancer Inst.,* 88:1091–1092, 1996.
Hanahan and Folkman, *J. Natl. Cancer Inst.,* 88:1091–1092, 1996.
Harland and Weintraub, *J. Cell Biol.,* 101:1094–1099, 1985.
Hay et al., *J. Mol. Biol.,* 175:493–510, 1984.
Hearing and Shenk, *J. Mol. Biol.* 167:809–822, 1983.
Hearing et al., *J. Virol.,* 67:2555–2558, 1987.
Hohenester et al., *EMBO J.,* 17:1656–1664.
Hollstein et al., *Science,* 253:49–53, 1991.
Holmgren, O'Reilly, Folkman, *J. Natl. Med.,* 1:149–153, 1995.
Hunt et al., *Proc. Natl. Acad. Sci. USA,* 83:3786–3790, 1986.
Hussussian et al., *Nature Genetics,* 15–21, 1994.
Jain, "Quantitative angiogenesis assays," progress and problems," *Nature Medicine,* 3:1203–1208, 1997.
Joki, et al., *Human Gene Ther.,* 6:1507–1513, 1995.
Kageyama, et al., *J. Biol. Chem.,* 262(5):2345–2351, 1987.
Kakeji and Teicher, *Invest. New Drugs,* 15:39–48, 1997.
Kamb et al., *Nature Genetics,* 8:22–26, 1994.
Kamb et al., *Science,* 2674:436–440, 1994.
Kaneda et al., *Science,* 243:375–378, 1989.
Kaplitt et al., *Arm. Thor. Surg.,* 62:1669–1676, 1996.
Kaplitt et al., *Nat. Genet.,* 8:148–153, 1994.
Kato et al, *J. Biol. Chem.,* 266:3361–3364, 1991.
Klagsbrun and D'Amore, *Annual Rev. Physiol.,* 53:217–239, 1991.
Kerbel, "Inhibition of tumor angiogenesis as a strategy to circumvent required resistance to anti-cancer therapeutic agents," *Bioassays,* 13:31–36, 1991.
Kerbel, *Bioessays,* 13:31–36, 1991.
Kessler et al., *Proc. Natl. Acad. Sci. USA,* 93:14082–14087, 1996.
Klein et al., *Nature,* 327:70–73, 1987.
Koeberl et al., *Proc. Natl. Acad. Sci. USA,* 94:1426–1431, 1997.
Korhonen, et al., Blood, Vol. 86, No. 5, Sep. 1, 1995: pp 1828–1835.
Levrero et al., *Gene,* 101: 195–202, 1991., 1989.
Macejak and Sarnow, *Nature,* 353:90–94, 1991.
Mann et al., *Cell,* 33:153–159, 1983., 1992.
Mauceri et al., "Combined effects of angiostatin and ionizing radiation in antitumour therapy," *Nature,* 394:287–291, 1998.
McCown et al., *Brain Res.,* 713:99–107, 1996.
Mizukami et al., *Virology,* 217:124–130, 1996.
Mori et al., *Cancer Res.,* 54:3396–3397, 1994.
Myers, EPO 0273085
Nicolas and Rubenstein, *In: Vectors: A survey of molecular cloning vectors and their uses,* Rodriguez and Denhardt (eds.), Stoneham: Butterworth, pp. 493–513, 1988.
Nicolau and Sene, *Biochim. Biophys. Acta,* 721:185–190, 1982.
Nicolau et al., *Methods Enzymol.,* 149:157–176, 1987.
Nobori et al., *Nature,* 368:753–756, 1995.
O'Reilly et al., "Endostatin: an endogenous inhibitor of angiogenesis and tumor growth,"*Cell,* 88:277–285, 1997.
O'Reilly et al., *Cell,* 79:315–328, 1994.
O'Reilly et al., *Cell,* 88:277–285, 1997.
O'Reilly, et al., *J. Natl. Med.,* 2:689–692, 1996.
Okamoto et al., *Proc. Nat'l Acad. Sci. USA,* 91:11045–11049, 1994.
Olivierio, et al., *EMBO J.,* 6(7):1905–1912, 1987.
Orlow et al., *Cancer Res.,* 54:2848–2851, 1994.
Pape and Kim, *Mol. Cell. Biol.,* 974–982, 1989.
Paskind et al., *Virology,* 67:242–248, 1975.
Pelletier and Sonenberg, *Nature,* 334:320–325, 1988.
Perales et al., *Proc. Natl. Acad. Sci.* 91:4086–4090, 1994.
Ping et al., *Microcirculation,* 3:225–228, 1996.
Poli and Cortese, *Proc. Natl. Acad. Sci. USA,* 86:8202–8206, 1989.
Potter et al., *Proc. Nat. Acad. Sci. USA,* 81:7161–7165, 1984.
Prowse and Baumann, *Mol Cell Biol,* 8(1):42–51, 1988.
Radler et al., *Science,* 275:810–814, 1997.
Rak, St Croix, Kerbel, *Anticancer Drugs,* 6:3–18, 1995.
Renan, *Radiother. Oncol.,* 19:197–218, 1990.
Ridgeway, *In: Vectors: A survey of molecular cloning vectors and their uses,* Rodriguez R L, Denhardt D T, ed., Stoneham:Butterworth, pp. 467–492, 1988.
Rippe et al., *Mol. Cell Biol.,* 10:689–695, 1990.
Ron, et al., *Mol. Cell. Biol.,* 2887–2895, 1991.
Roux et al., *Proc. Natl Acad. Sci. USA,* 86:9079–9083, 1989.
Sambrook et al., In Molecular Cloning: A Laboratory Manual. pp. 1.53–1.110, Cold Spring Harbor Laboratory Press, Cold Spring Harbor, N.Y., 1989.
Samulski et al., *J. Virol.,* 61(10):3096–3101, 1987.
Serrano et al., *Nature,* 366:704–707, 1993.
Serrano et al., *Science,* 267:249–252, 1995.
Sim et al., *Cancer Res.,* 57:1329–1334, 1997.
Speigelman, et al., *J. Biol. Chem.,* 264(3), 1811–1815, 1989.
Sugarbaker, *Curr. Prob. Cancer* 3:1–59, 1979;
Suit, "The scope of the problem of primary tumor control, *Cancer,* 61:2141–2147, 1988.
Teicher, Sotomayor, Huang, *Cancer Res.,* 52:6702–6704, 1992.
Temin, *In: Gene Transfer,* Kucherlapati (ed.), New York: Plenum Press, pp. 149–188, 1986.
Tibbetts *Cell,* 12:243–249, 1977.
Tur-Kaspa et al., *Mol. Cell Biol.,* 6:716–718, 1986.Umbas et al., *Cancer Res.,* 52:5104
Wagner et al., *Proc. Natl. Acad. Sci.* 87(9):3410–3414, 1990.
Wagner et al., *Science,* 260:1510–1513, 1993.

Walther and Stein, *J. Mol. Med*, Vol. 74, 1996: pp. 379–392.
Watt et al., *Proc. Natl Acad. Sci.*, 83(2): 3166–3170, 1986.
Weichselbaum et al., *Proc. Natl. Acad. Sci. USA*, 83:2684–2688, 1986.
Weichselbaum Hallahan, Sukhalme, Kufe, "Gene therapy targeted by ionizing radiation," *Int. J. Radiant Oncol. Biol. Phys.*, 24:565–567, 1992.
Weichselbaum, Beekett, Dahlberg, Dritschilo, *Int. J. Radiat. Oncol. Biol. Phys.*, 14:907–912, 1988.
Weidner et al., *Am J Pathol;* 143:401–409, 1993
Weidner et al., *N Engl J Med;* 324: 1–8, 1991
Weidner, "Tumoural vascularity as a prognostic factor in cancer patients: the evidence continues to grow," *J. Pathol.*, 184:119–122, 1998.
Weinberg, *Science*, 254:1138–1145, 1991.
Wilson, et al., *Mol. Cell. Biol.*, 6181–6191, 1990.
Wong et al., *Gene*, 10:87–94, 1980.
Wu and Wu, *Adv. Drug Delivery Rev.*, 12:159–167, 1993.
Wu and Wu, *Biochem.*, 27:887–892, 1988.
Wu and Wu, *J. Biol. Chem.*, 262:4429–4432, 1987.
Xiao et al., *J. Virol.*, 70:8098–8108, 1996.
Yang et al., *Proc. Natl. Acad. Sci USA*, 87:9568–9572, 1990.
Zechner, et al., *Mol. Cell. Biol.*, 2394–2401, 1988.

What is claimed is:

1. The method of inhibiting the growth of a cell, said method comprising the steps of:
   (a) first contacting said cell with anti-angiogenic protein factor selected from the group consisting of angiostatin and endostatin in an amount effective to sensitize said cell to ionizing radiation; and then
   (b) exposing said cell to a dose of ionizing radiation effective to inhibit the growth of said cell.

2. The method of claim 1, wherein said anti-angiogenic protein factor is angiostatin.

3. The method of claim 1, wherein said anti-angiogenic protein factor is endostatin.

4. The method of claim 1, further comprising contacting said cell with IL-12.

5. The method of claim 1, wherein said cell is a tumor endothelial cell.

6. The method of claim 5, wherein said cell is located within an animal, and said contacting comprises in vivo delivery of said anti-angiogenic protein factor.

7. The method of claim 6, wherein said contacting is effected by direct injection of said cell with said anti-angiogenic protein factor.

8. The method of claim 6, wherein said contacting is effected by regional delivery of said anti-angiogenic protein factor.

9. The method of claim 6, wherein said contacting is effected by local delivery of said anti-angiogenic protein factor.

10. The method of claim 6, wherein said contacting comprises delivering said anti-angiogenic factor endoscopically, intratracheally, intralesionally, percutaneously, intravenously, subcutaneously or intratumorally.

11. The method of claim 6, further comprising the step of tumor resection, prior to, after or during said contacting.

12. The method of claim 5, wherein said tumor endothelial cell is a human tumor endothelial cell.

13. The method of claim 12, wherein said cell is a brain cancer endothelial cell.

14. The method of claim 12, wherein said cell is a breast cancer endothelial cell.

15. The method of claim 1, wherein said anti-angiogenic protein factor is administered 2 days prior to said radiation.

16. The method of claim 1, wherein said anti-angiogenic protein factor is administered 1 day prior to said radiation.

17. The method of claim 1, wherein said anti-angiogenic protein factor is administered 12 hours prior to said radiation.

18. The method of claim 1, wherein said anti-angiogenic protein factor is administered 6 hours prior to said radiation.

19. The method of claim 1, wherein said anti-angiogenic protein factor is administered 3 hours prior to said radiation.

20. The method of claim 1, wherein said anti-angiogenic protein factor is administered 1 hour prior to said radiation.

21. The method of claim 1, wherein said anti-angiogenic protein factor is administered 30 minutes prior to said radiation.

22. The method of claim 1, wherein said anti-angiogenic protein factor is administered 15 minutes prior to said radiation.

23. The method of claim 1, wherein said anti-angiogenic protein factor is administered immediately prior to said radiation.

24. The method of claim 1, wherein said ionizing radiation is X-radiation, γ-radiation, or β-radiation.

25. The method of claim 1, wherein said cell is resistant to anti-angiogenic protein factor therapy.

26. The method of claim 1, wherein said cell is resistant to radiotherapy.

27. The method of claim 1, further comprising the step of contacting said cell with a chemotherapeutic agent.

28. The method of claim 27, wherein said chemotherapeutic agent is selected from the group consisting of adriamycin, 5-fluorouracil (5FU), etoposide (VP-16), camptothecin, actinomycin-D, mitomycin C, cisplatin (CDDP), doxorubicin, etoposide, verapamil, podophyllotoxin, carboplatin, procarbazine, mechlorethamine, cyclophosphamide, ifosfamide, melphalan, chlorambucil, bisulfan, nitrosurea, dactinomycin, daunorubicin, bleomycin, plicomycin, mitomycin, tamoxifen, taxol, transplatinum, vincristin, vinblastin and methotrexate.

* * * * *

UNITED STATES PATENT AND TRADEMARK OFFICE
CERTIFICATE OF CORRECTION

PATENT NO.    : 6,420,335 B1
DATED         : July 16, 2002
INVENTOR(S)   : Ralph R. Weichselbaum et al.

It is certified that error appears in the above-identified patent and that said Letters Patent is hereby corrected as shown below:

<u>Title page,</u>
Item [22], substitute "Jun. 16, 1999" and replace with -- Jun. 15, 1999 -- therefor.

Signed and Sealed this

Twenty-fifth Day of March, 2003

JAMES E. ROGAN
*Director of the United States Patent and Trademark Office*

UNITED STATES PATENT AND TRADEMARK OFFICE
CERTIFICATE OF CORRECTION

PATENT NO.   : 6,420,335 B1                                              Page 1 of 1
DATED        : July 16, 2002
INVENTOR(S)  : Ralph R. Weichselbaum et al.

It is certified that error appears in the above-identified patent and that said Letters Patent is hereby corrected as shown below:

<u>Column 47,</u>
Line 27, after "with" please insert -- an -- therefor.

Signed and Sealed this

Eighth Day of July, 2003

JAMES E. ROGAN
*Director of the United States Patent and Trademark Office*